(12) United States Patent
Nishio et al.

(10) Patent No.: US 9,883,937 B2
(45) Date of Patent: Feb. 6, 2018

(54) METHOD AND APPARATUS FOR TREATING URETHRAL STRICTURE

(71) Applicant: TERUMO KABUSHIKI KAISHA, Shibuya-ku (JP)

(72) Inventors: Kosuke Nishio, Machida (JP); Riyaheh Arastoo, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 138 days.

(21) Appl. No.: 14/451,912

(22) Filed: Aug. 5, 2014

(65) Prior Publication Data

US 2015/0327981 A1    Nov. 19, 2015

Related U.S. Application Data

(60) Provisional application No. 61/994,499, filed on May 16, 2014.

(51) Int. Cl.
*A61F 2/04*    (2013.01)
*A61F 2/00*    (2006.01)
(Continued)

(52) U.S. Cl.
CPC .............. *A61F 2/04* (2013.01); *A61F 2/0063* (2013.01); *A61F 2/82* (2013.01); *A61F 2/848* (2013.01);
(Continued)

(58) Field of Classification Search
CPC .. A61F 2/04–2/07; A61F 2002/041–2002/077; A61F 2/82–2/92;
(Continued)

(56) References Cited

U.S. PATENT DOCUMENTS 4,771,773 A * 9/1988 Kropf ...................... A61F 2/95
606/108
5,108,416 A * 4/1992 Ryan ...................... A61F 2/958
604/103.05
(Continued)

FOREIGN PATENT DOCUMENTS

WO    2011/076390 A1    6/2011

OTHER PUBLICATIONS

"Suction Cup Tape." Suction Cup Tape. N.p., Jul. 23, 2012. Web. Jan. 6, 2016. <http://www.inventables.com/technologies/suction-cup-tape>.*
(Continued)

*Primary Examiner* — Catherine B Kuhlman
(74) *Attorney, Agent, or Firm* — Buchanan Ingersoll & Rooney PC

(57) ABSTRACT

A method of delivering a therapeutic device to a treatment area of a body lumen, the therapeutic device including a) a delivery member possessing at least one attachment part and b) a treatment membrane, includes wrapping the treatment membrane on the delivery member, attaching the treatment membrane to the attachment part of the delivery member, and moving the delivery member toward the treatment area, detaching the treatment membrane from the delivery member, and withdrawing the delivery member from the body lumen.

8 Claims, 36 Drawing Sheets

Figure 2A:
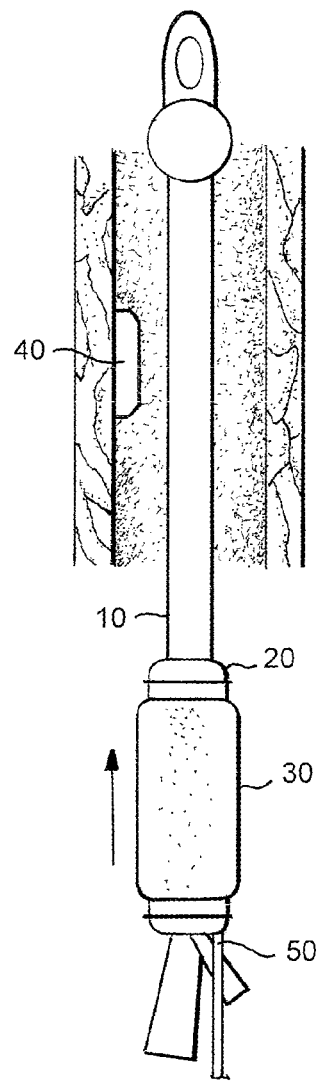

(51) Int. Cl.
| | |
|---|---|
| *A61F 2/92* | (2013.01) |
| *A61F 2/848* | (2013.01) |
| *A61F 2/95* | (2013.01) |
| *A61F 2/82* | (2013.01) |
| *B29C 65/00* | (2006.01) |
| *B29L 31/00* | (2006.01) |
| *A61M 25/10* | (2013.01) |
| *A61F 2/958* | (2013.01) |
| *A61M 25/00* | (2006.01) |

(52) U.S. Cl.
CPC .............. *A61F 2/92* (2013.01); *A61F 2/95* (2013.01); *A61M 25/10* (2013.01); *A61M 25/1029* (2013.01); *B29C 66/4322* (2013.01); *A61F 2/958* (2013.01); *A61F 2002/0072* (2013.01); *A61F 2002/047* (2013.01); *A61F 2002/9583* (2013.01); *A61F 2220/005* (2013.01); *A61F 2220/0016* (2013.01); *A61F 2220/0075* (2013.01); *A61M 25/0017* (2013.01); *A61M 2025/1015* (2013.01); *A61M 2025/1031* (2013.01); *A61M 2025/1054* (2013.01); *A61M 2025/1081* (2013.01); *A61M 2025/1086* (2013.01); *B29L 2031/7543* (2013.01); *Y10T 29/49838* (2015.01); *Y10T 29/49909* (2015.01); *Y10T 156/1038* (2015.01)

(58) Field of Classification Search
CPC ............ A61F 2/95; A61F 2/105; A61F 2002/9505–2002/9665; A61F 2/243–2/2439; A61M 2025/1086
See application file for complete search history.

(56) References Cited

U.S. PATENT DOCUMENTS

| | | | | |
|---|---|---|---|---|
| 5,779,732 | A * | 7/1998 | Amundson | A61F 2/88 606/198 |
| 5,902,228 | A * | 5/1999 | Schulsinger | A61F 2/062 128/897 |
| 5,957,929 | A * | 9/1999 | Brenneman | A61F 2/92 606/1 |
| 6,475,232 | B1 * | 11/2002 | Babbs | A61F 2/07 623/1.13 |
| 6,939,381 | B2 | 9/2005 | Stark et al. | |
| 7,559,953 | B2 * | 7/2009 | Sarac | A61F 2/2415 600/36 |
| 7,771,463 | B2 * | 8/2010 | Ton | A61F 2/88 623/1.11 |
| 2002/0007222 | A1 | 1/2002 | Desai | |
| 2006/0047336 | A1 * | 3/2006 | Gale | A61F 2/958 623/1.11 |
| 2007/0088431 | A1 * | 4/2007 | Bourang | A61F 2/2433 623/2.11 |
| 2008/0027528 | A1 | 1/2008 | Jagger et al. | |

OTHER PUBLICATIONS

Communication and Search Report dated Apr. 28, 2016 issued in the corresponding European Patent Application No. 15178973.2-1654 (11 pages).
Yidong Liu et al., "One-stage dorsal inlay oral mucosa graft urethroplasty for anterior urethral stricture", BMC Urology, BIOMED Central, London, GB, vol. 14, No. 1, May 8, 2014, p. 35, XP021186366, ISSN: 1471-2490, DOI: 10.1186/1471-2490-14-35 (6 pages).
S. Tritschler et al., "Praputialhaut als freies Transplantat", Der Urologe A, May 1, 2013, pp. 668-671, XP055266441, DOI: 10.1007/s00120-013-3120-x (4 pages).

* cited by examiner

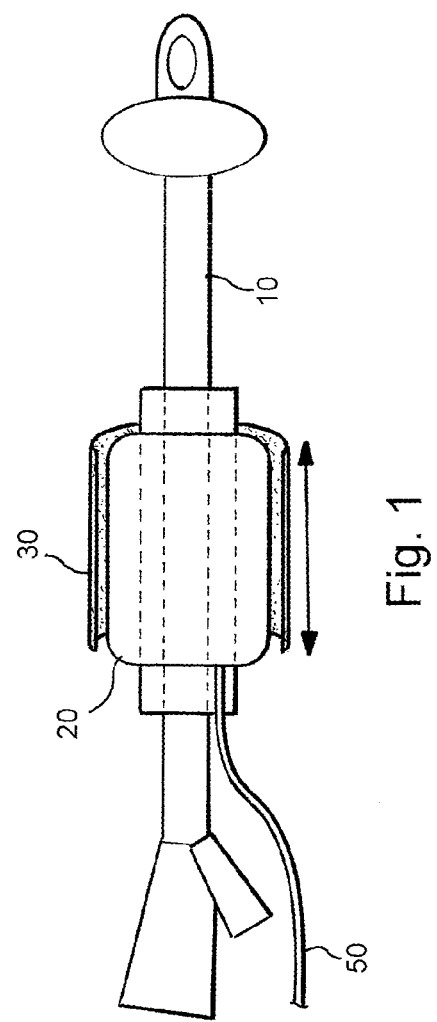

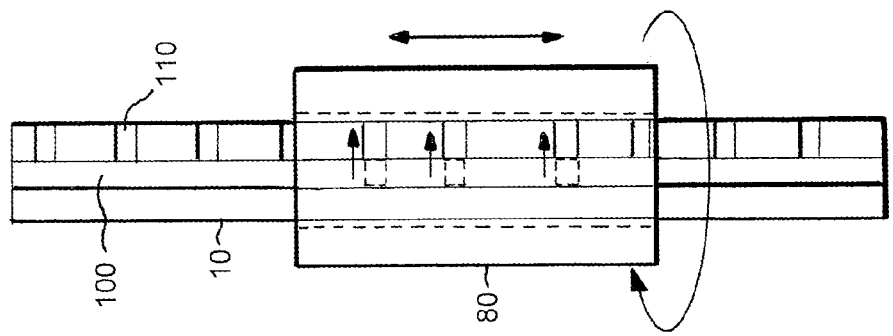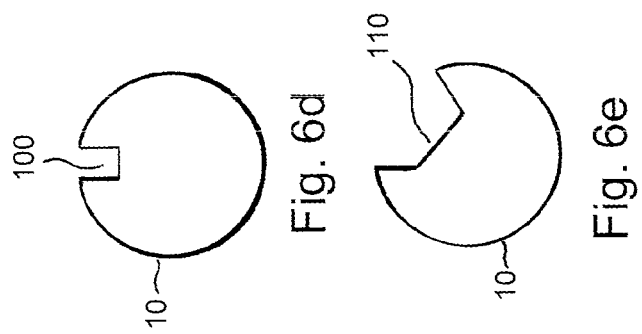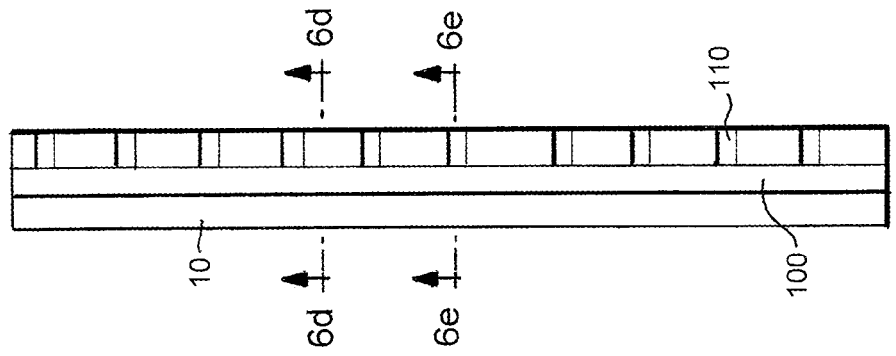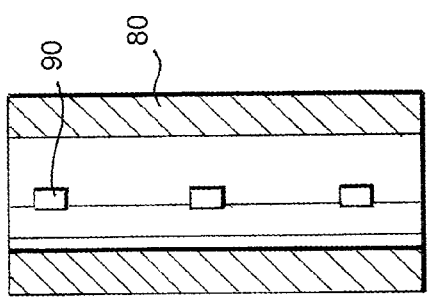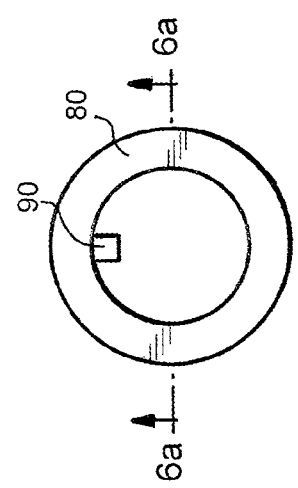

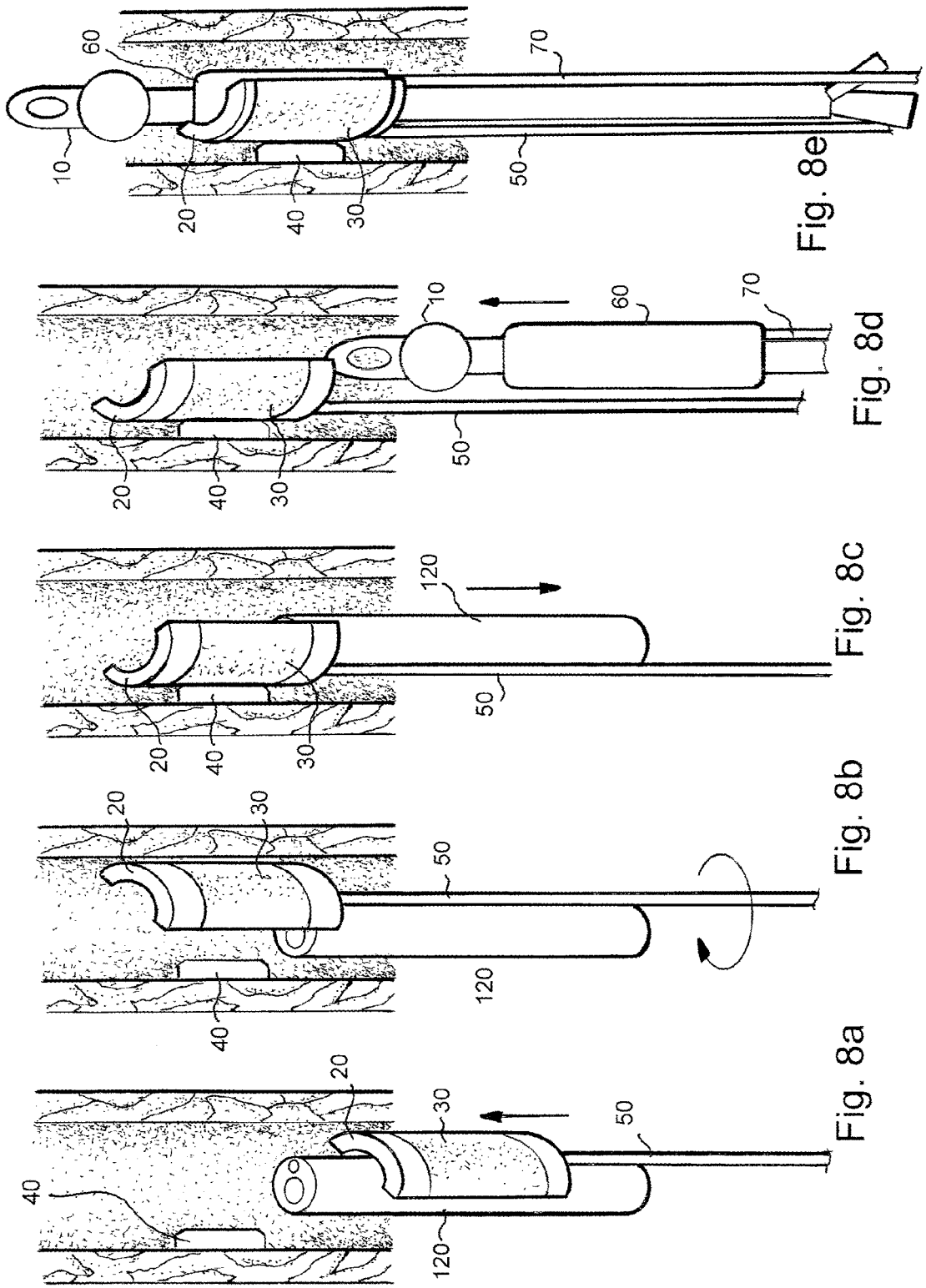

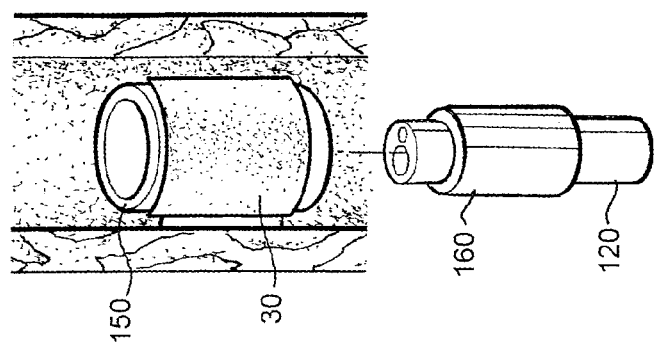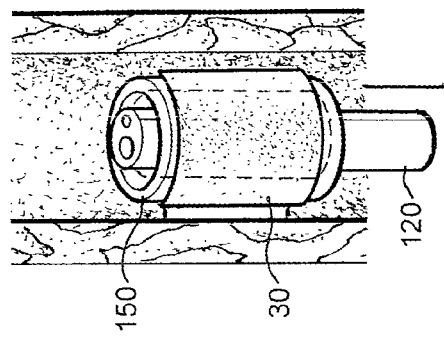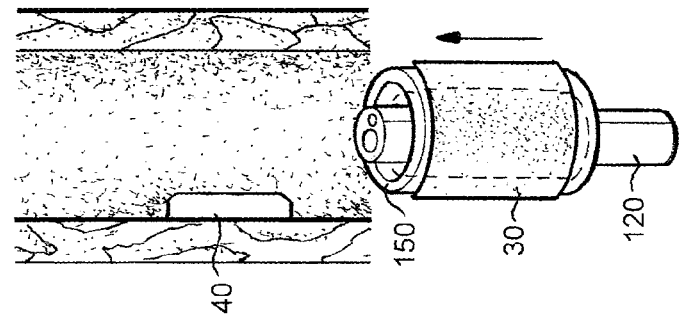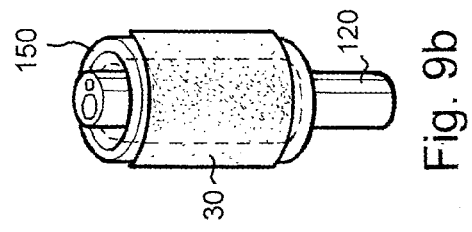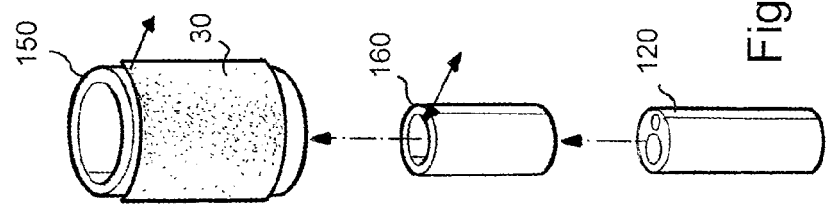

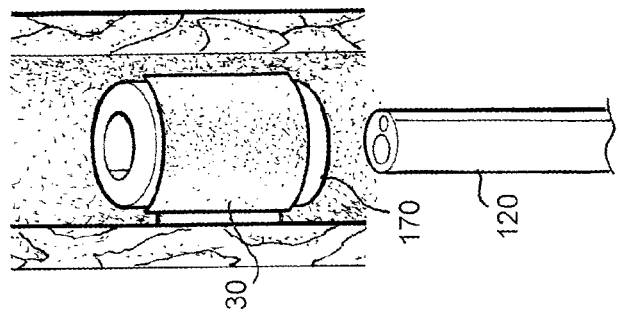
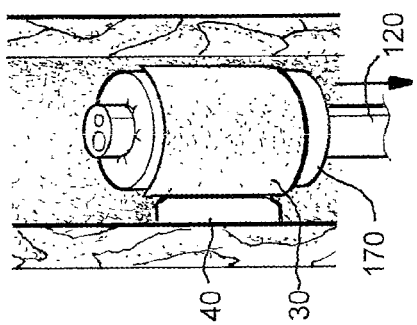
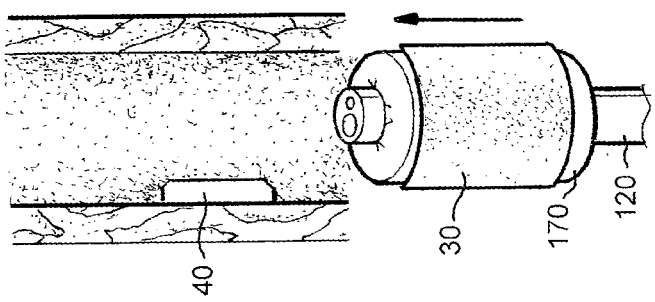
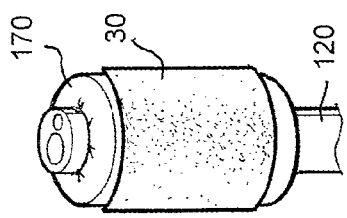
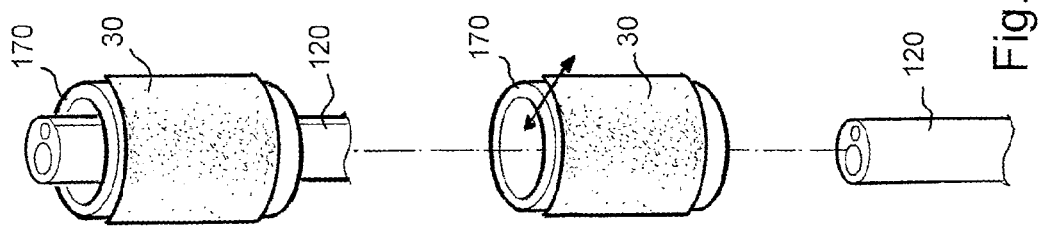

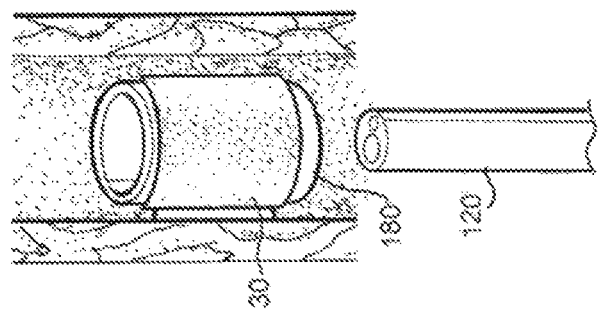
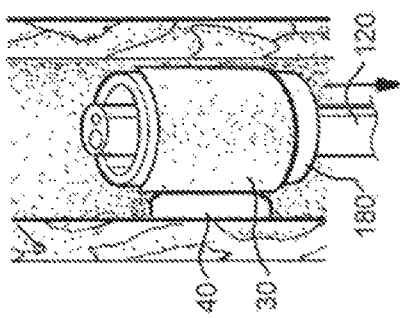
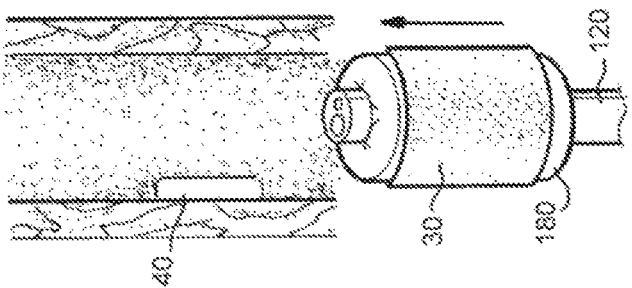
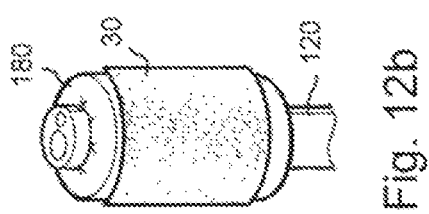
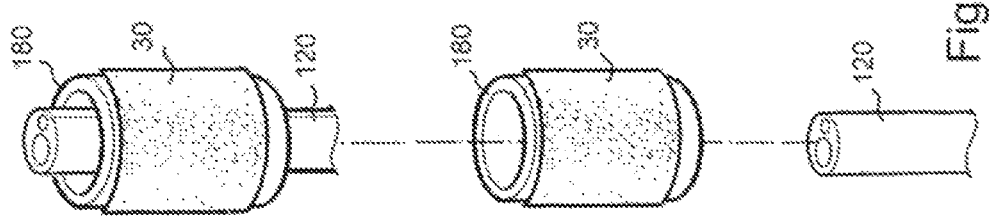

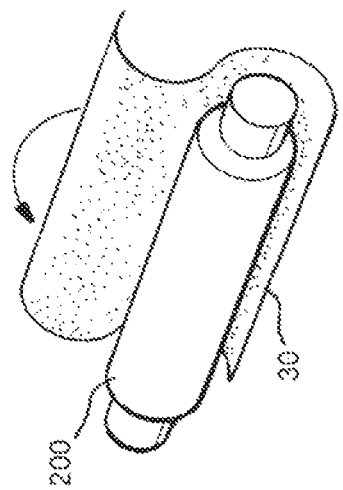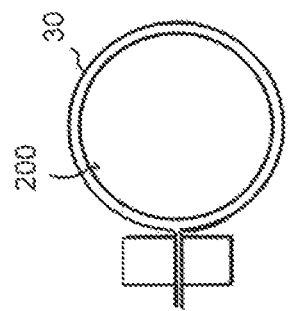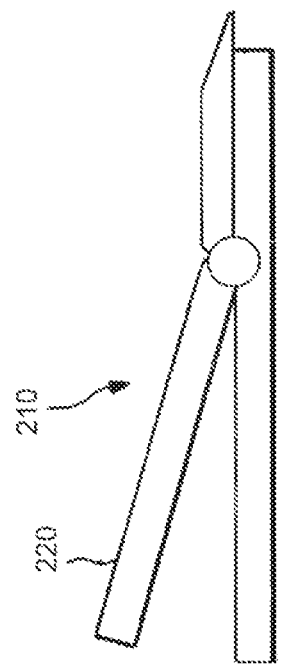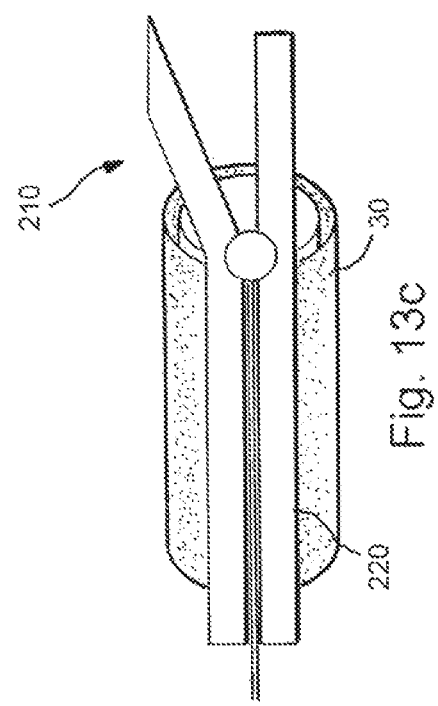

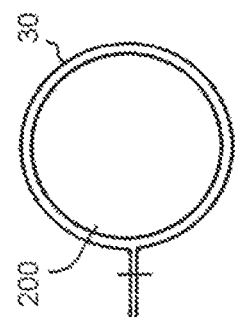
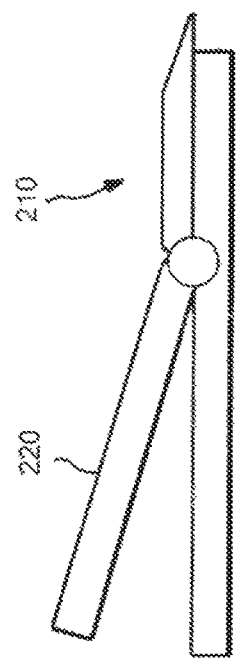
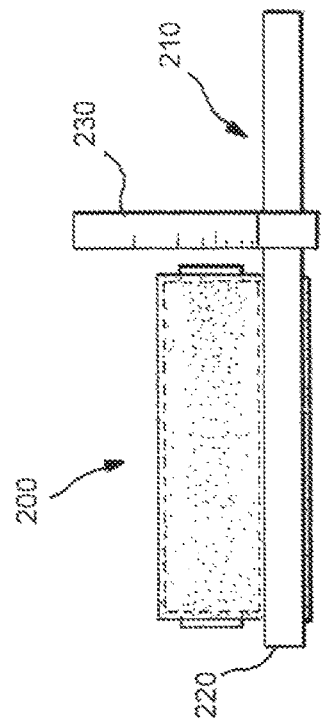
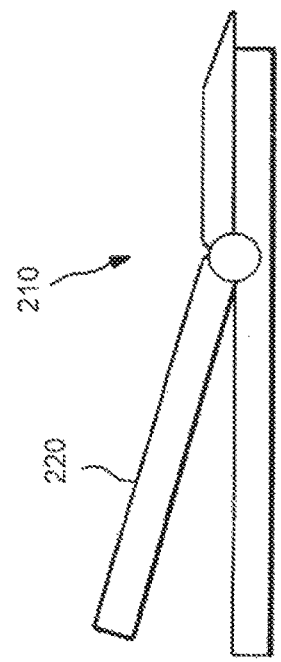

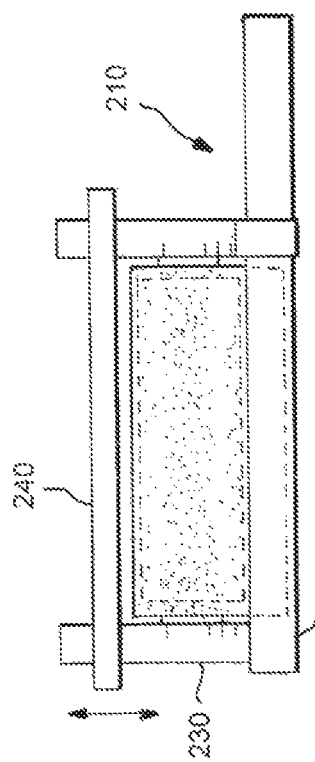
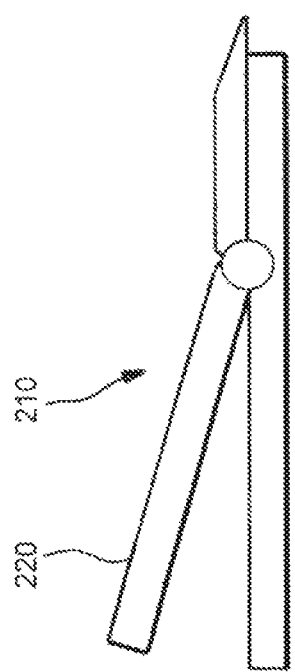

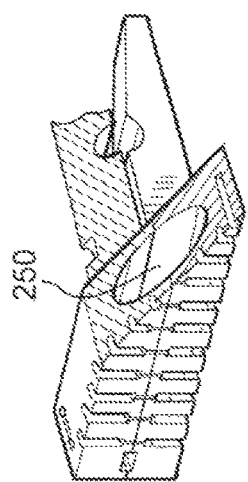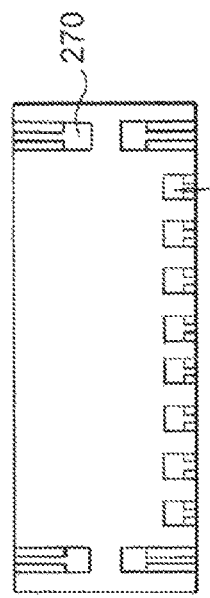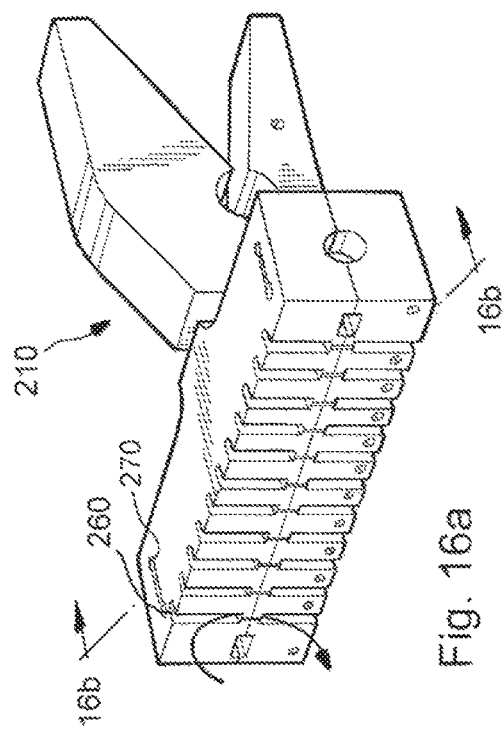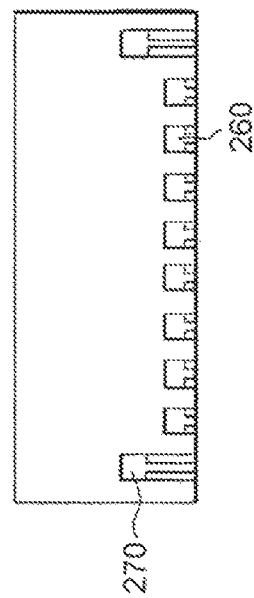

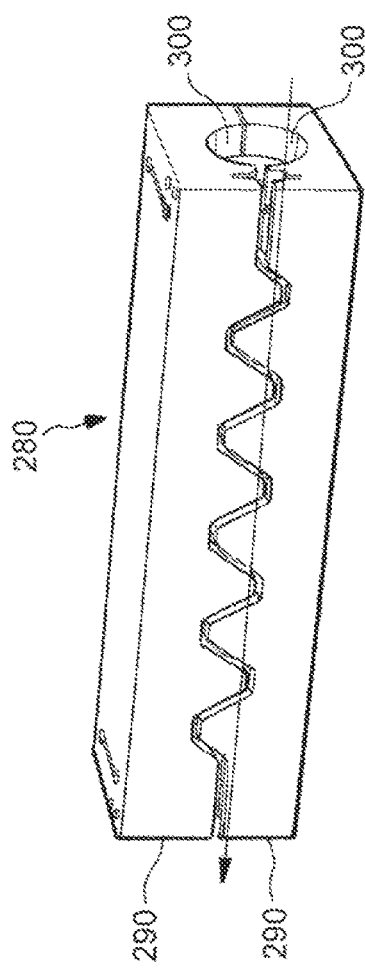
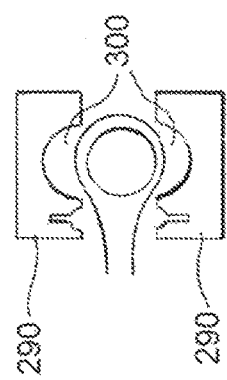
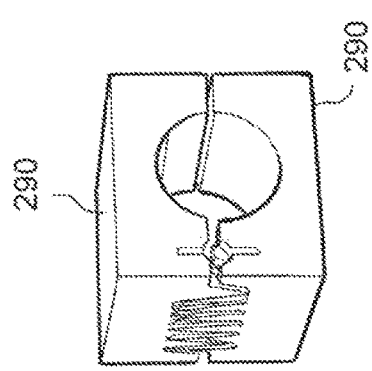

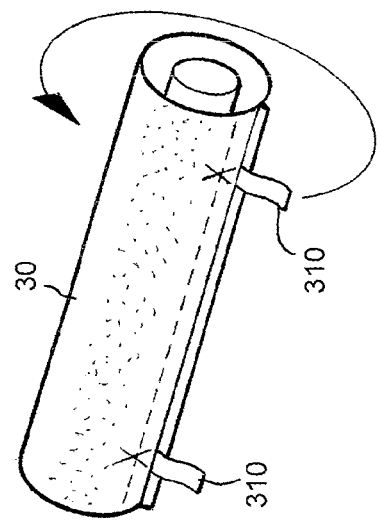
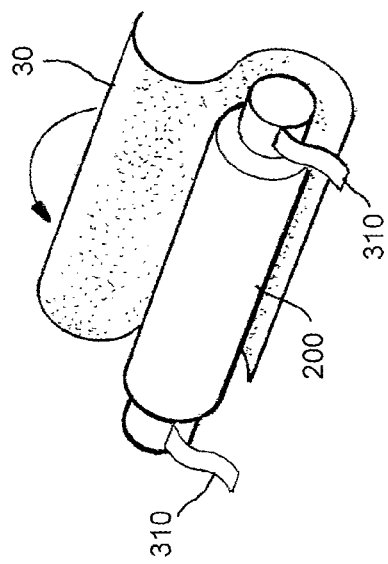

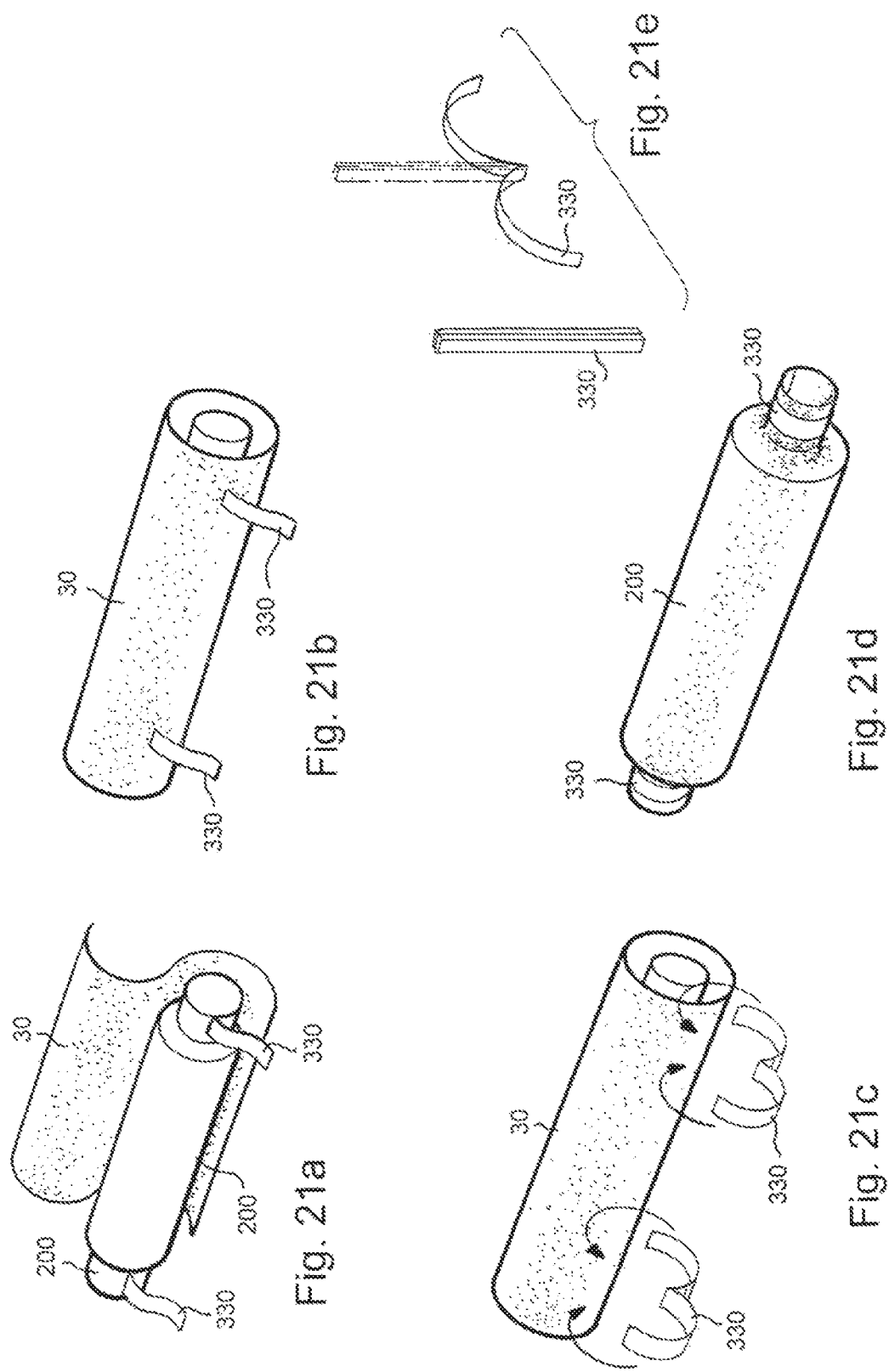

 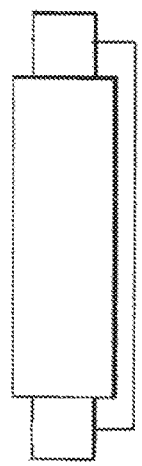   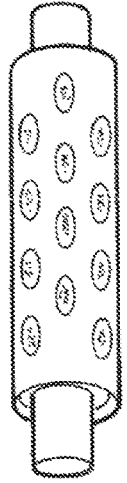
Fig. 23f  Fig. 23g  Fig. 23h  Fig. 23i  Fig. 23j
 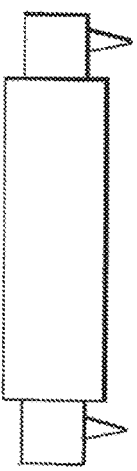 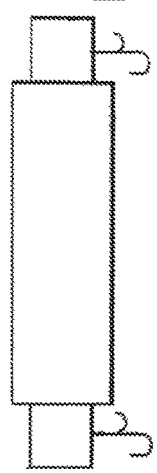 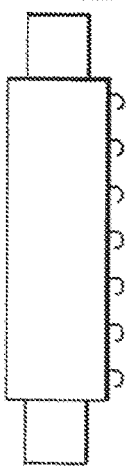 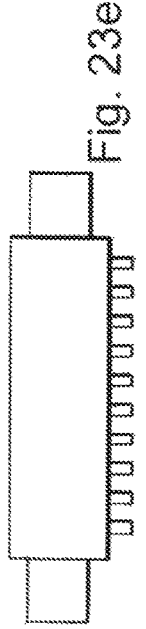
Fig. 23a  Fig. 23b  Fig. 23c  Fig. 23d  Fig. 23e

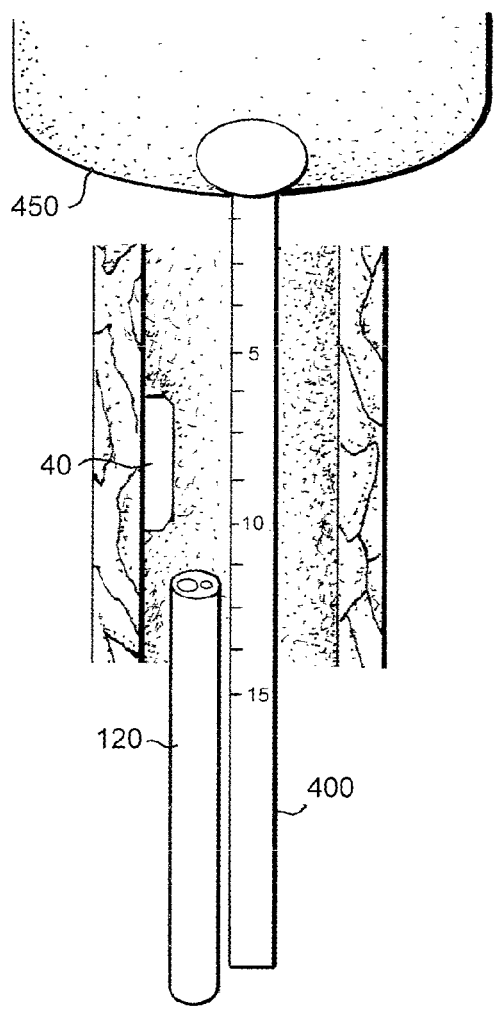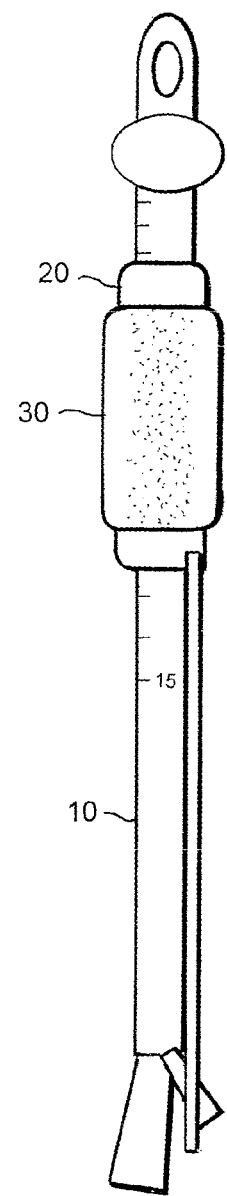
Fig. 24 a
Fig. 24b

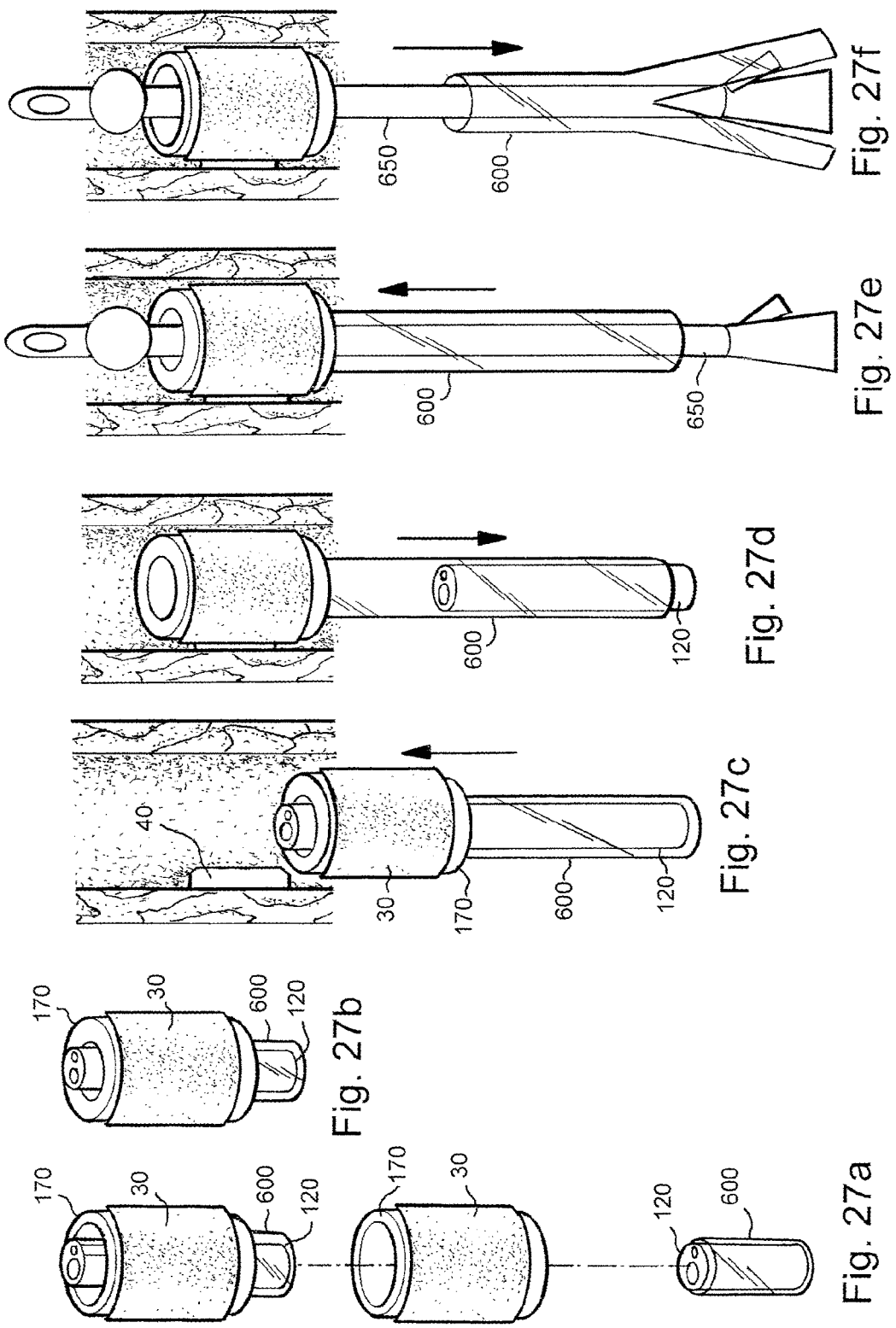

METHOD AND APPARATUS FOR TREATING URETHRAL STRICTURE

CROSS-REFERENCE TO RELATED APPLICATIONS

The present application claims the benefit under 35 U.S.C. §119(e) to U.S. Provisional Application No. 61/994,499 filed on May 16, 2014, the entire content of which is incorporated by reference herein.

TECHNOLOGICAL FIELD

The disclosure here pertains generally to a method and apparatus for treating urethral stricture. More particularly, the disclosure is directed to a trans-urethral urethroplasty method and apparatus.

BACKGROUND DISCUSSION

Known treatment options for urethral stricture, which is an abnormal narrowing of the urethra, include urethroplasty surgery as well as minimally invasive procedures such as dilation, stent implantation, and urethrotomy. Due to the invasiveness of urethroplasty surgery, it is only recommended in extreme cases of urethral stricture. However, minimally invasive procedures currently in use to treat urethral stricture can be of limited long-term effectiveness because they do not promote epithelial function at the treatment site. Accordingly, a need exists for a practical, minimally invasive treatment of urethral stricture which promotes epithelial function at the treatment site.

SUMMARY

One aspect of the disclosure here involves a method of treating a treatment area of a body lumen, the method including inserting an elongated member into the body lumen, wherein the elongated member is configured to guide a delivery member, the delivery member possessing an outer portion on which is mounted a treatment membrane, moving the delivery member to the treatment area, contacting the treatment membrane mounted on the delivery member with the treatment area for a predetermined period of time, and withdrawing the delivery member from the treatment area after the predetermined period of time.

Another aspect involves a method of mounting a treatment membrane to a delivery member, the method including wrapping the treatment membrane around the delivery member, pinching opposite overlapped edges of the treatment membrane together, and attaching the opposite overlapped edges of the treatment membrane together.

A further aspect of the disclosure involves a method of delivering a therapeutic device to a treatment area of a body lumen, the therapeutic device including a) a delivery member possessing at least one attachment part and b) a treatment membrane, the method including wrapping the treatment membrane on the delivery member, attaching the treatment membrane to the attachment part of the delivery member, and moving the delivery member toward the treatment area.

An additional aspect of the disclosure involves a method of delivering a therapeutic device to a treatment area of a body lumen, the therapeutic device including a) a delivery member and b) a treatment membrane attached to the delivery member, the method including wrapping the treatment membrane on the delivery member, moving the delivery member toward the treatment area, detaching the treatment membrane from the delivery member, and withdrawing the delivery member from the body lumen.

BRIEF DESCRIPTION OF THE DRAWING FIGURES

Additional features and aspects of the method and apparatus for treating urethral stricture disclosed here will become more apparent from the following detailed description considered with reference to the accompanying drawing figures in which like elements are designated by like reference numerals.

FIG. 1 is a schematic illustration of an apparatus for delivering a treatment membrane to a treatment area.

Figure 2B:
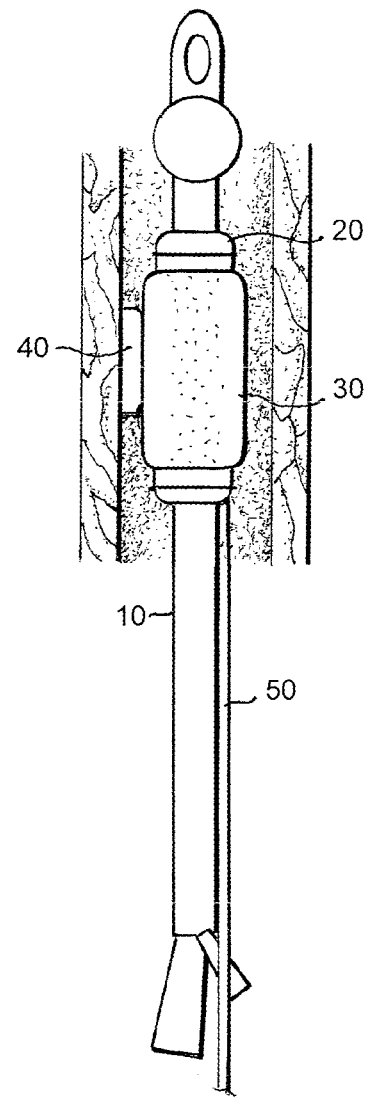

FIGS. 2(a)-2(b) illustrate an exemplary delivery procedure using the apparatus of FIG. 1.

Figure 3A:
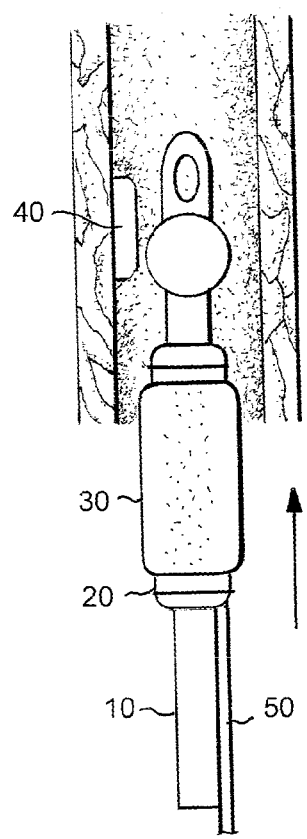
Figure 3B:
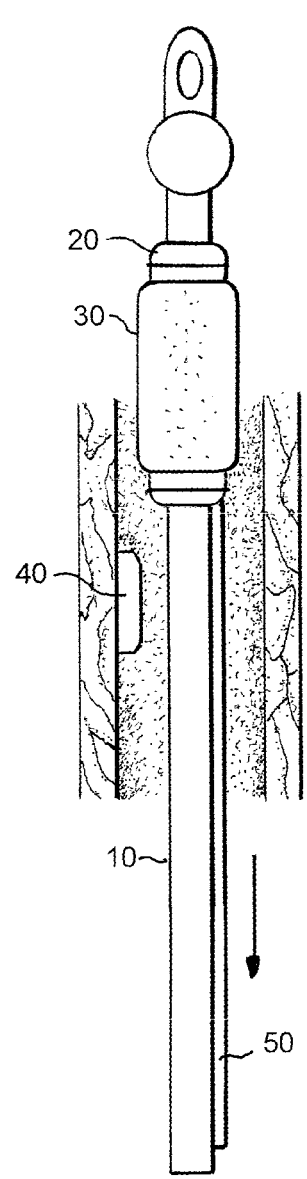
Figure 3C:
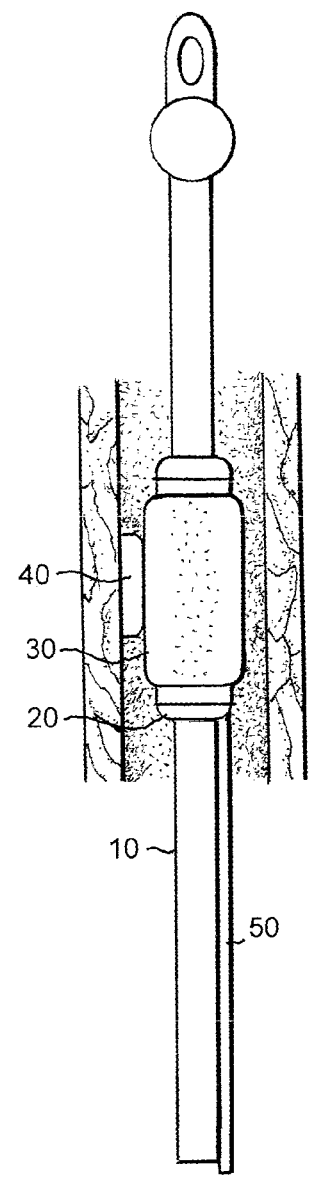

FIGS. 3(a)-3(c) illustrate an exemplary delivery procedure using the apparatus of FIG. 1.

Figure 4A:
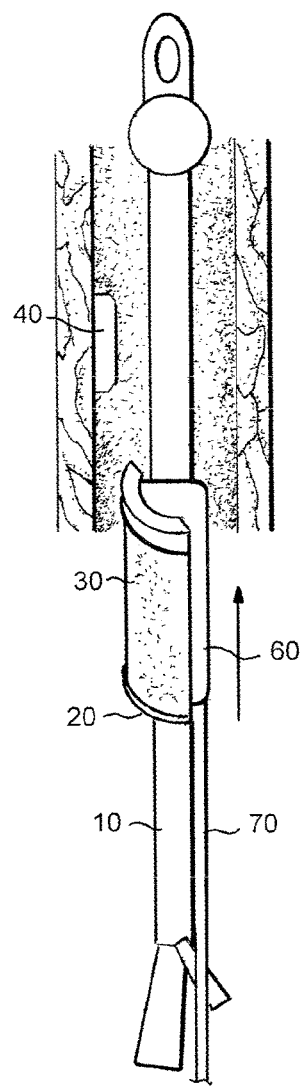
Figure 4B:
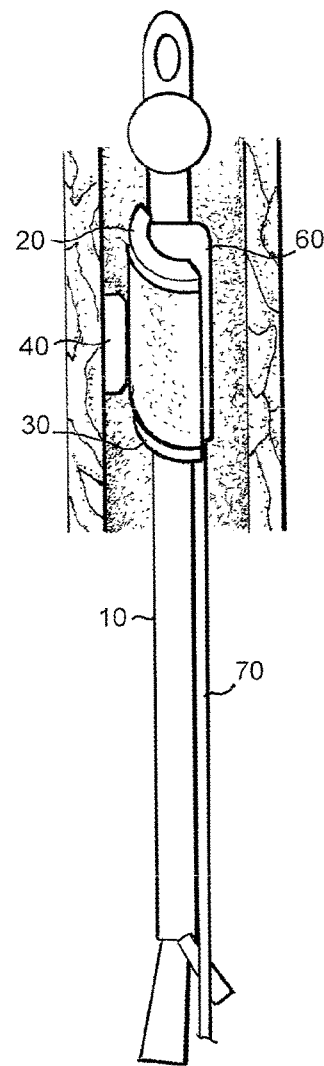
Figure 4C:
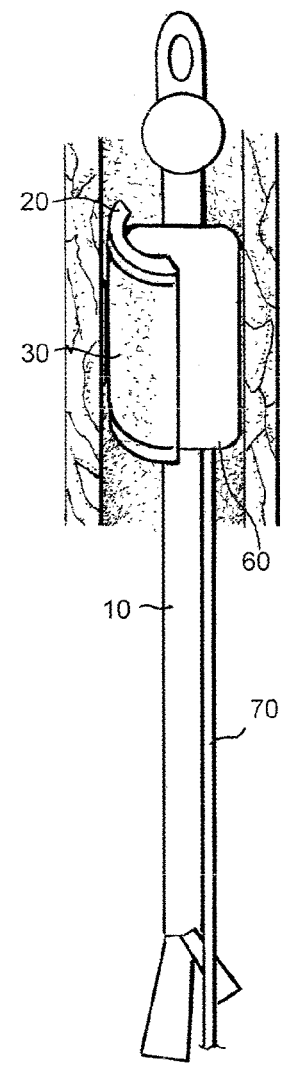
Figure 5D:
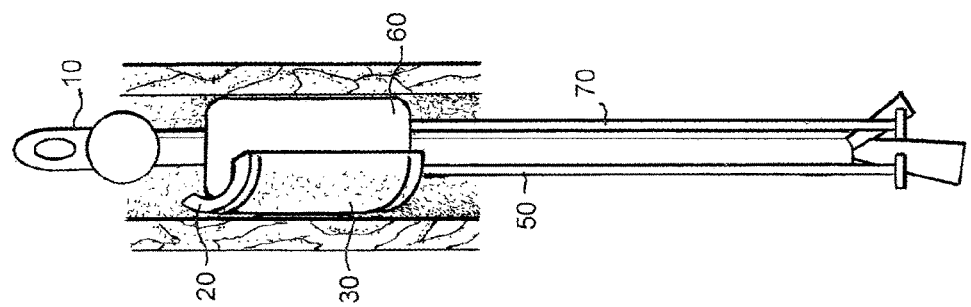
Figure 5C:
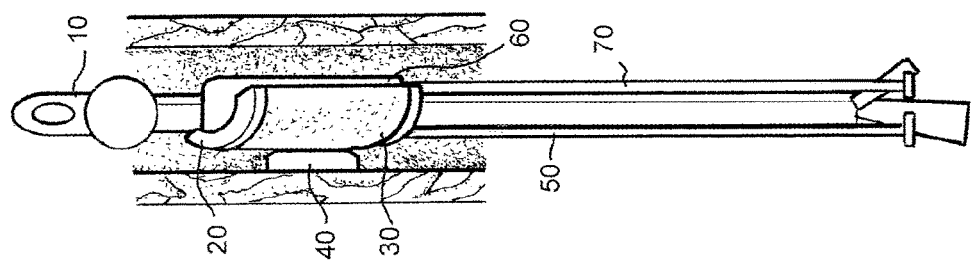
Figure 5B:
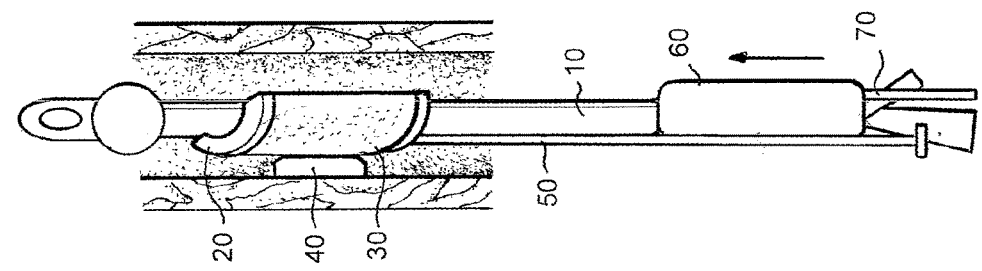
Figure 5A:
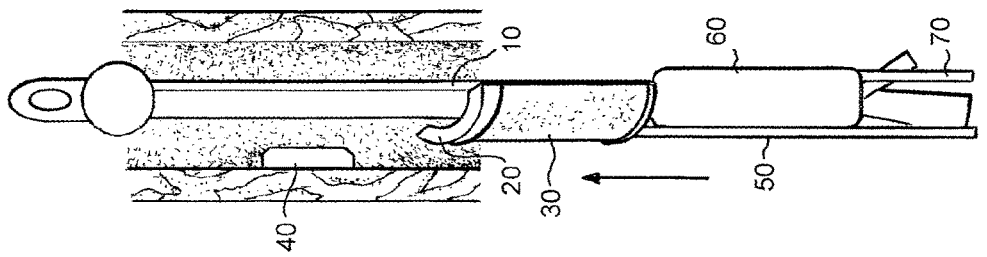
Figure 7D:
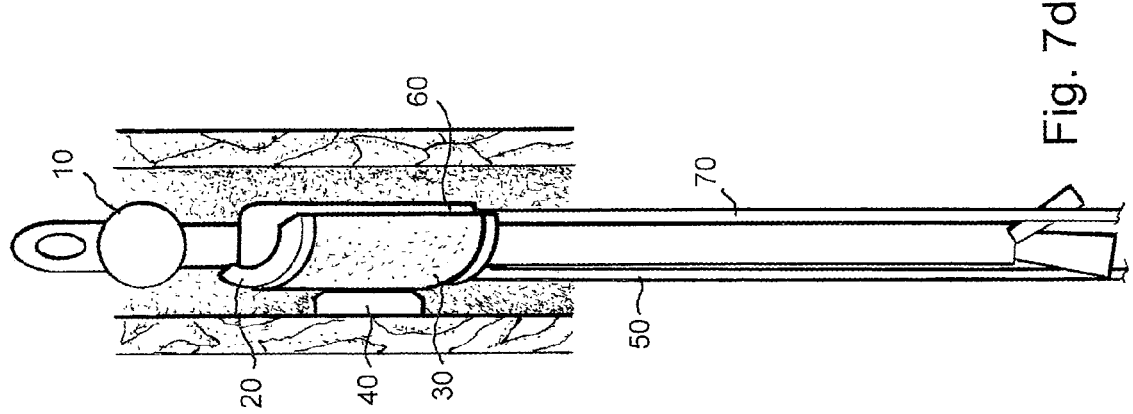
Figure 7C:
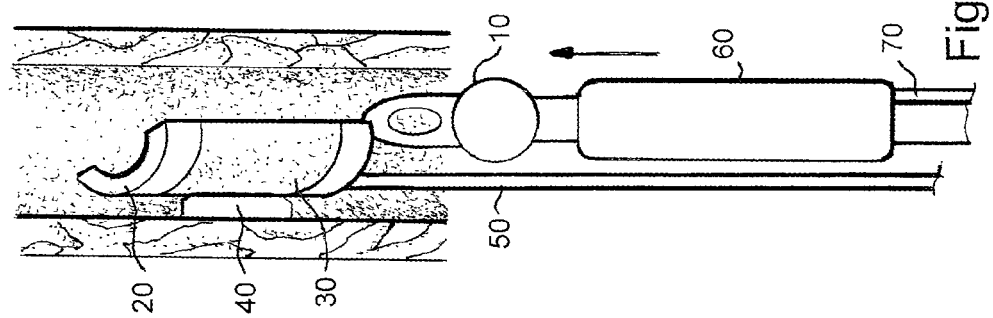
Figure 7B:
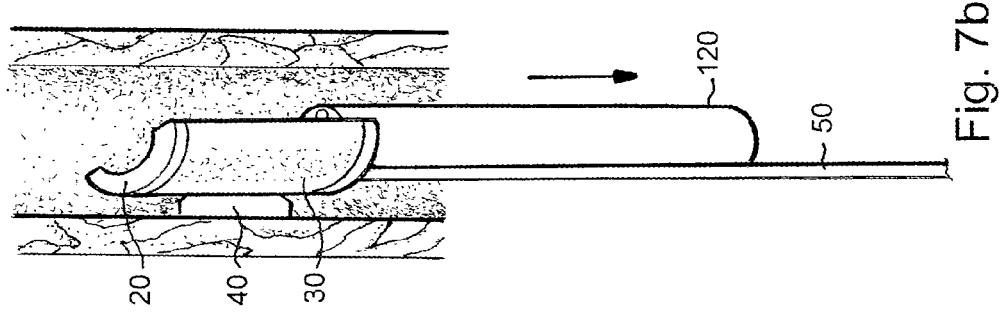
Figure 7A:
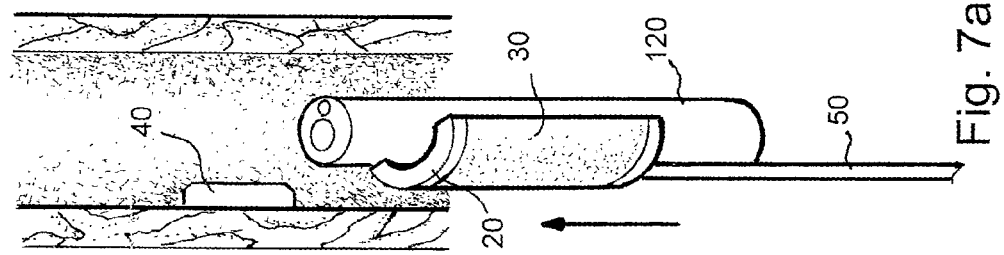
Figure 10E:
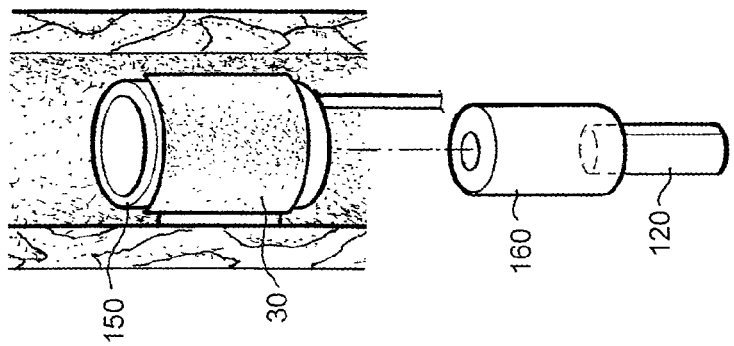
Figure 10D:
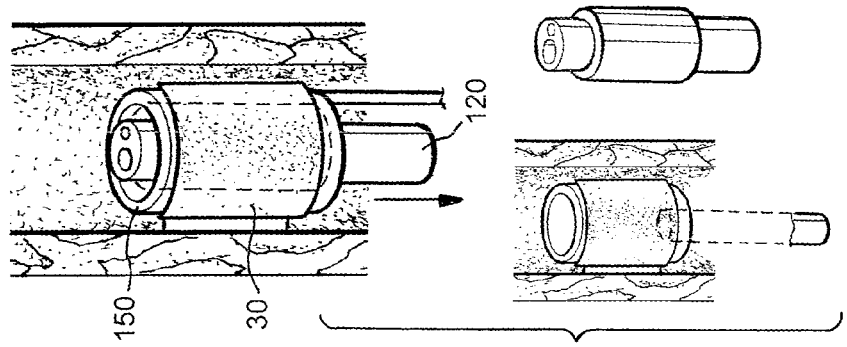
Figure 10C:
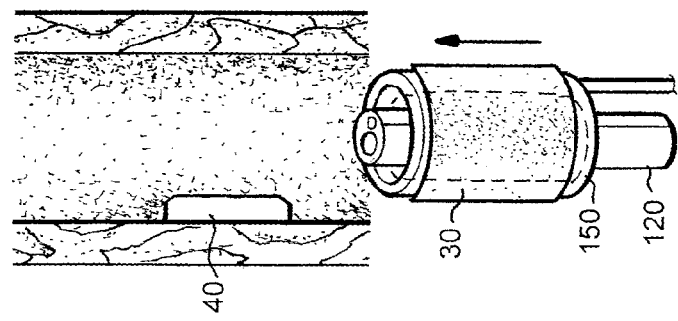
Figure 10B:
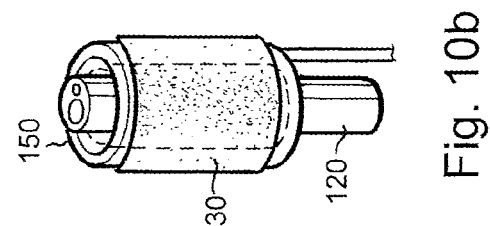
Figure 10A:
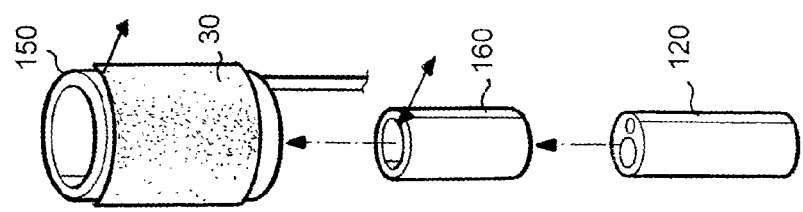

FIGS. 4(a)-4(c) illustrate an exemplary delivery procedure using an apparatus for delivering a treatment membrane to a treatment area.

FIGS. 5(a)-5(d) illustrate an exemplary delivery procedure using the apparatus of FIGS. 4(a)-4(c) for delivering a treatment membrane to a treatment area.

FIGS. 6(a)-6(f) illustrate an exemplary delivery procedure using an apparatus for delivering a treatment membrane to a treatment area.

FIGS. 7(a)-7(d) illustrate an exemplary delivery procedure using an apparatus for delivering a treatment membrane to a treatment area.

FIGS. 8(a)-8(e) illustrate an exemplary delivery procedure using the apparatus of FIGS. 7(a)-7(d) for delivering a treatment membrane to a treatment area.

FIGS. 9(a)-9(e) illustrate an exemplary delivery procedure using an apparatus for delivering a treatment membrane to a treatment area.

FIGS. 10(a)-10(e) illustrate an exemplary delivery procedure using an apparatus for delivering a treatment membrane to a treatment area.

FIGS. 11(a)-11(e) illustrate an exemplary delivery procedure using an apparatus for delivering a treatment membrane to a treatment area.

FIGS. 12(a)-12(e) illustrate an exemplary delivery procedure using an apparatus for delivering a treatment membrane to a treatment area.

FIGS. 13(a)-13(f) illustrate an exemplary mounting procedure using an apparatus for mounting a treatment membrane to a delivery member.

FIGS. 14(a)-14(b) illustrate an exemplary mounting procedure using an apparatus for mounting a treatment membrane to a delivery member.

FIGS. 15(a)-15(b) illustrate an exemplary mounting procedure using an apparatus for mounting a treatment membrane to a delivery member.

FIGS. 16(a)-16(d) illustrate an exemplary mounting procedure using an apparatus for mounting a treatment membrane to a delivery member.

FIGS. 17(a)-17(c) illustrate an exemplary mounting procedure using an apparatus for mounting a treatment membrane to a delivery member.

FIGS. 18(a)-18(b) illustrate an exemplary attaching procedure using an attachment part of a delivery member.

FIGS. 19(a)-19(d) illustrate an exemplary attaching and detaching procedure using an attachment part of a delivery member.

Figure 20B:
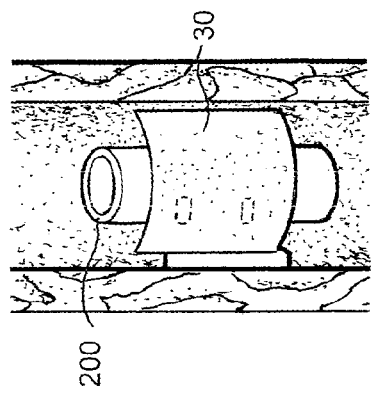
Figure 20A:
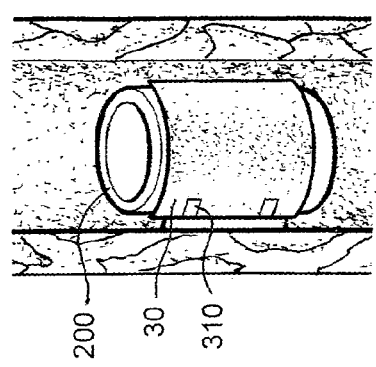

FIGS. 20(a)-20(b) illustrate an exemplary detaching procedure using an attachment part of a delivery member.

FIGS. 21(a)-21(e) illustrate an exemplary attaching and detaching procedure using an attachment part of a delivery member.

Figure 22:
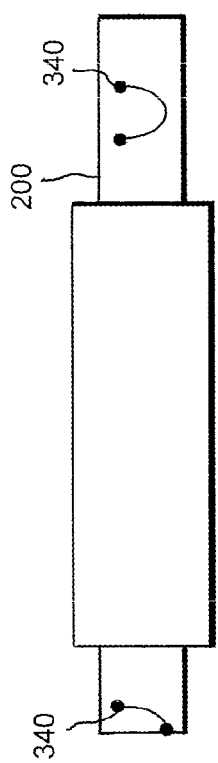

FIGS. 22 illustrates an attachment part of a delivery member.

FIGS. 23(a)-23(j) illustrate alternative attachment part embodiments.

Figure 24C:
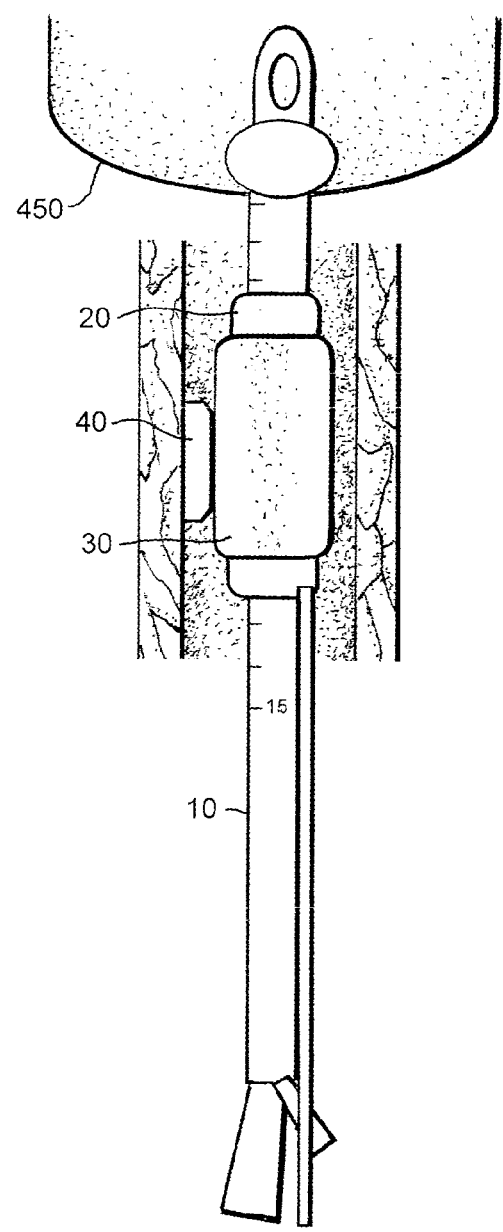

FIGS. 24(a)-24(c) illustrate an exemplary method and apparatus for positioning the delivery member relative to the treatment area.

Figure 25A:
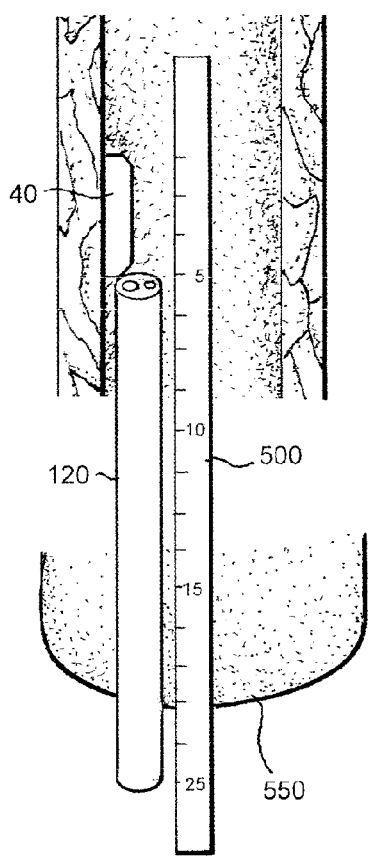
Figure 25B:
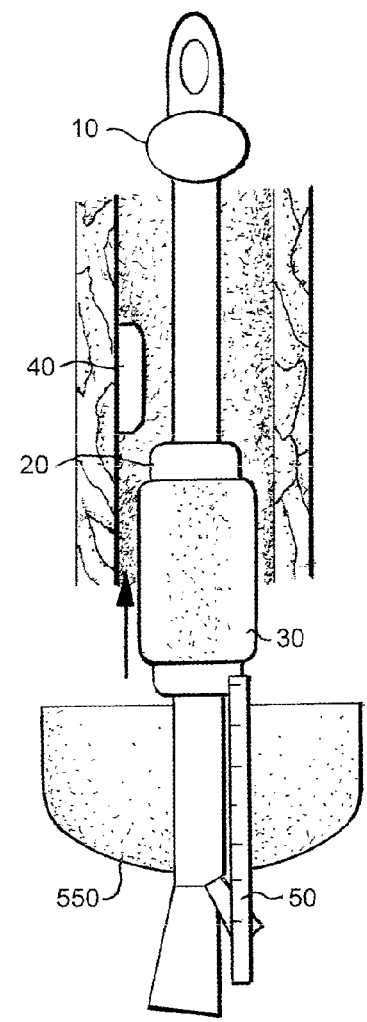
Figure 25C:
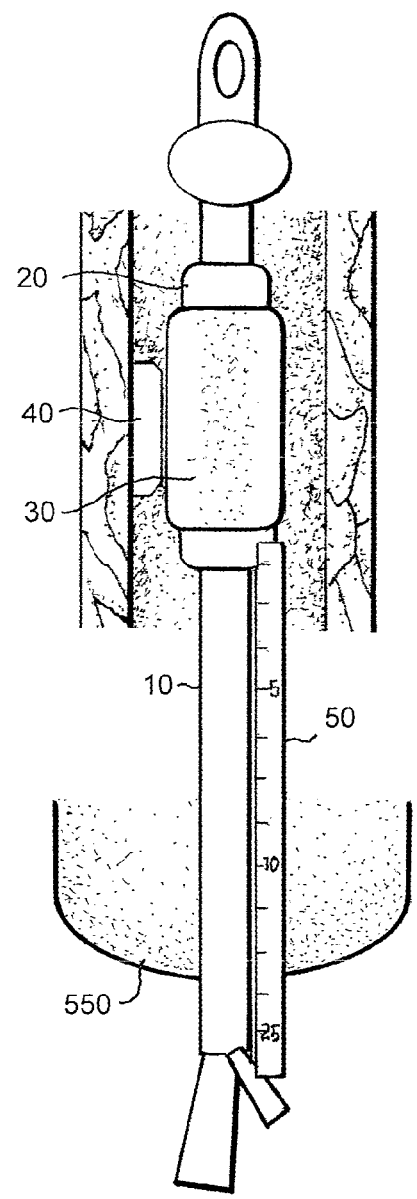

FIGS. 25(a)-25(c) illustrate another exemplary method and apparatus for positioning the delivery member relative to the treatment area.

Figure 26A:
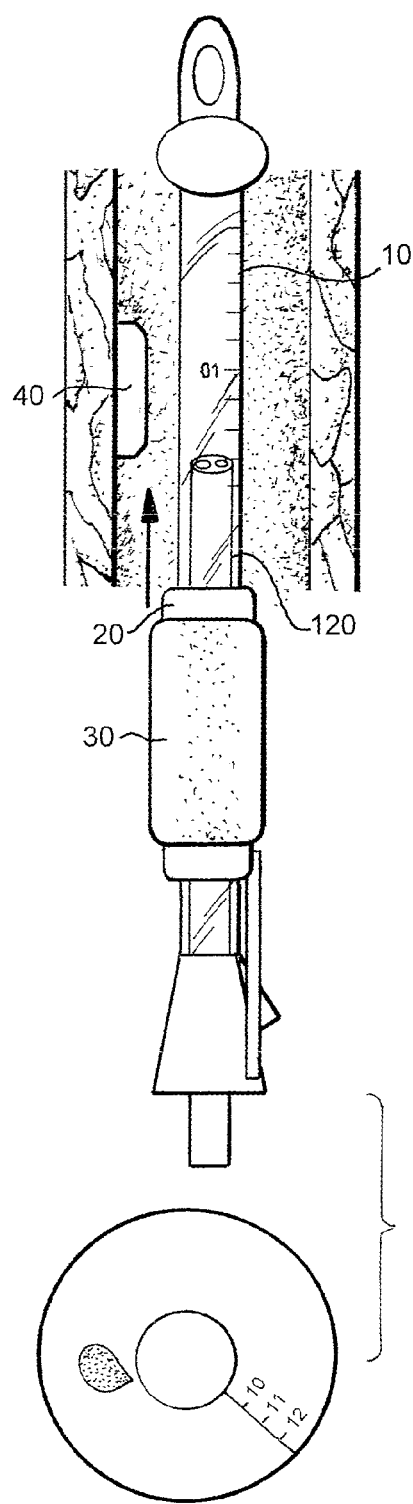
Figure 26B:
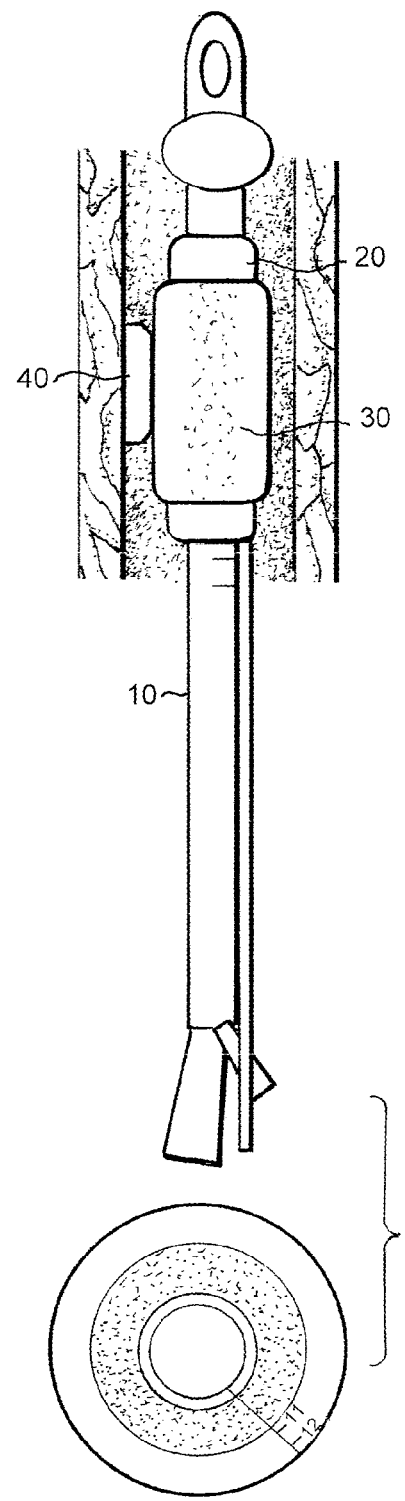

FIGS. 26(a)-26(b) illustrate another exemplary method and apparatus for positioning the delivery member relative to the treatment area.

FIGS. 27(a)-27(f) illustrate another exemplary method and apparatus for positioning the delivery member relative to the treatment area.

Figure 28A:
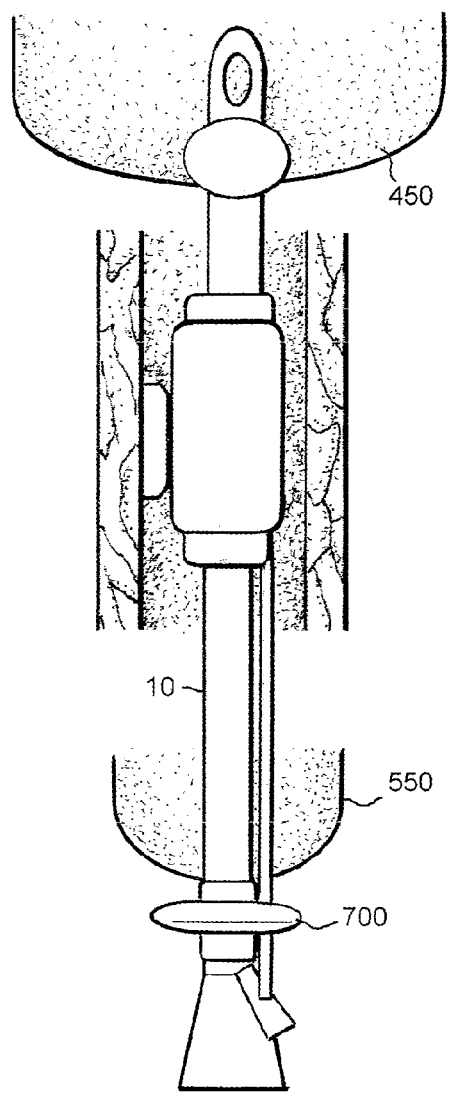
Figure 28B:
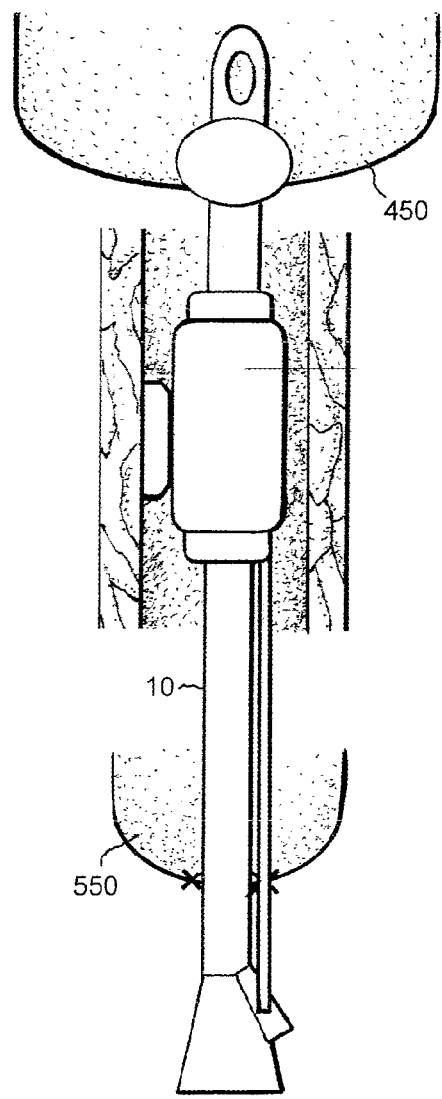
Figure 29D:
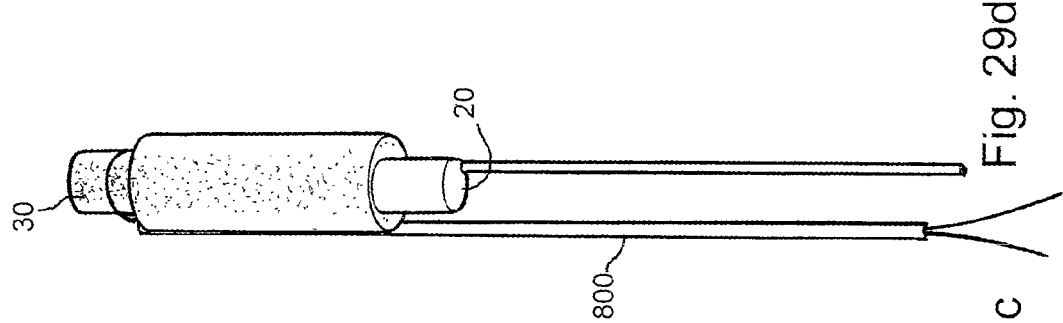
Figure 29C:
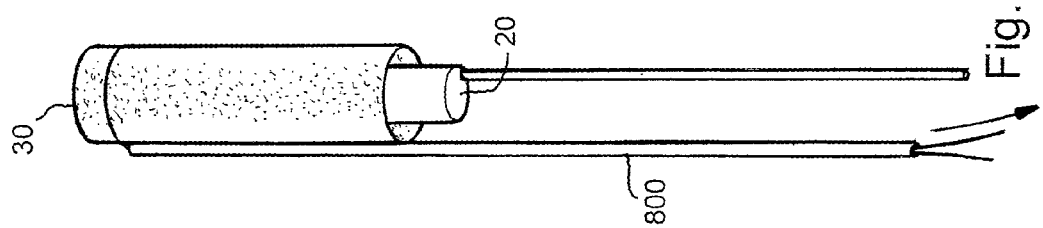
Figure 29B:
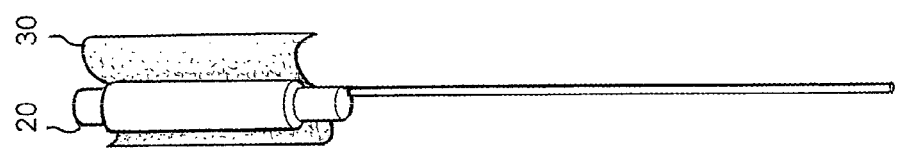
Figure 29A:
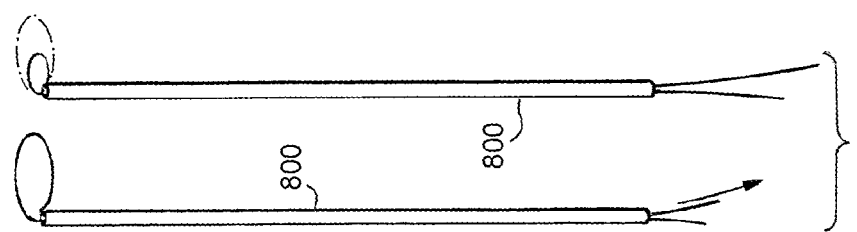
Figure 29H:
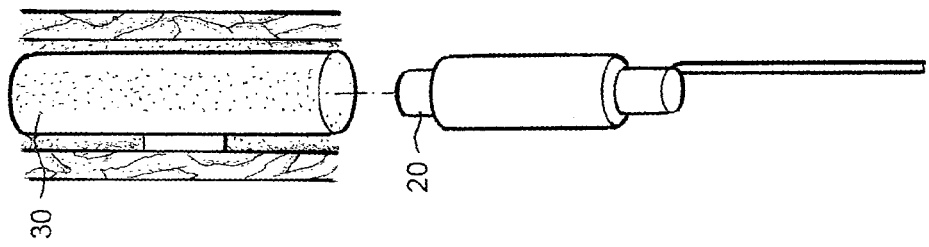
Figure 29G:
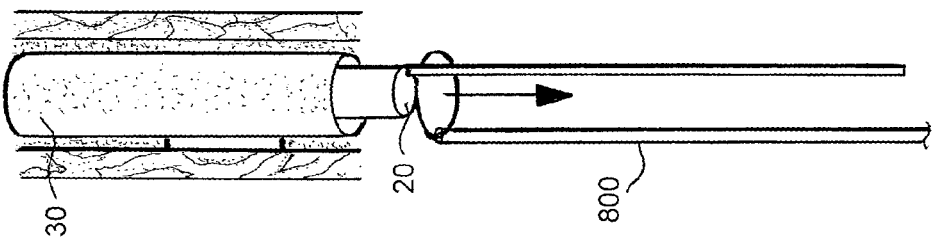
Figure 29F:
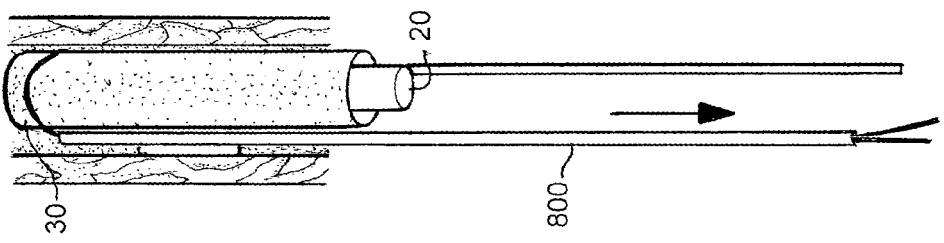
Figure 29E:
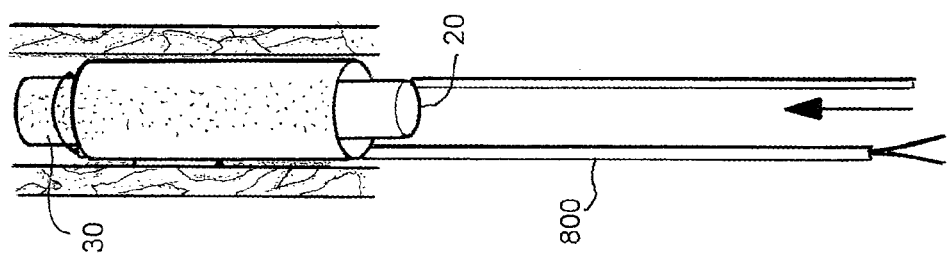
Figure 30C:
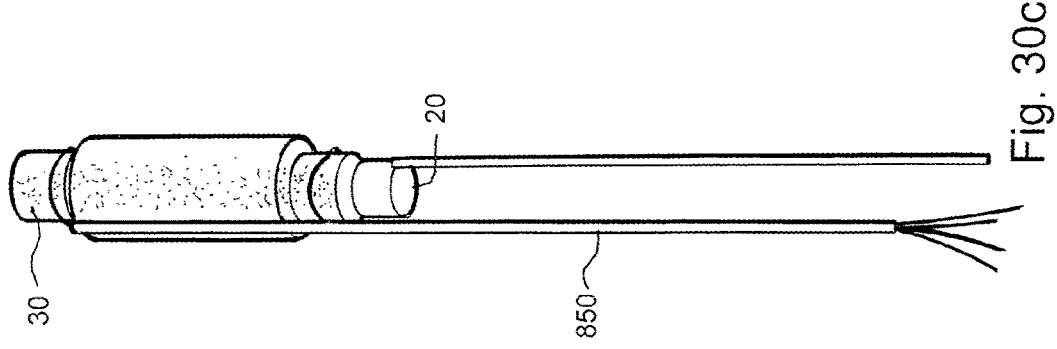
Figure 30B:
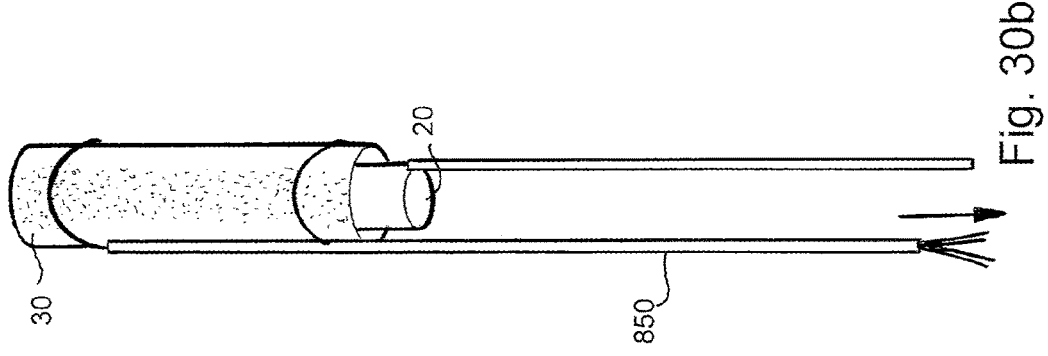
Figure 30A:
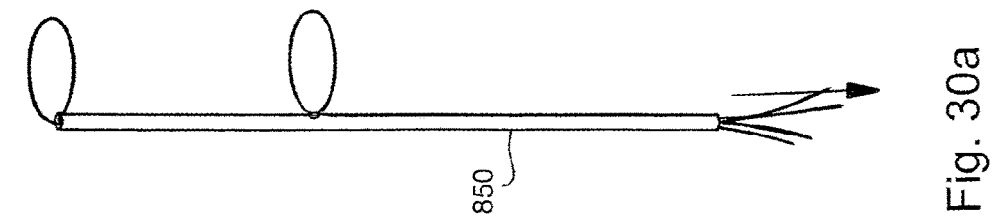
Figure 30H:
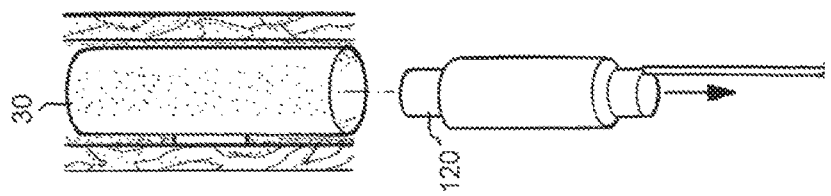
Figure 30G:
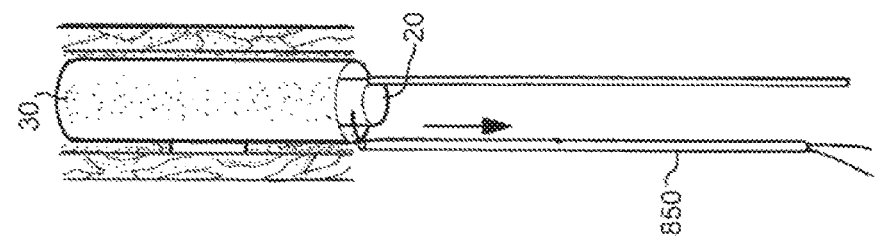
Figure 30F:
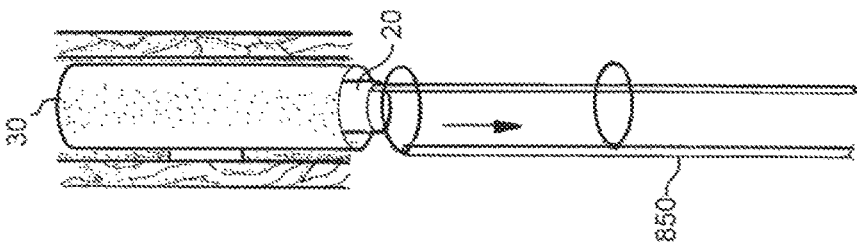
Figure 30E:
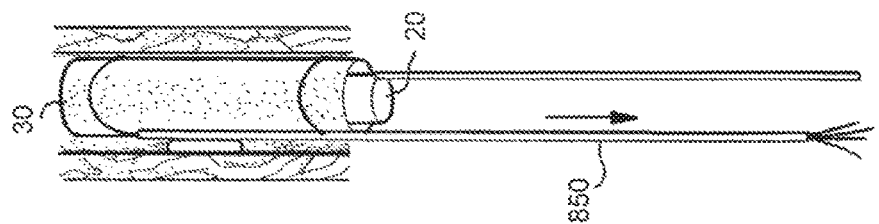
Figure 30D:
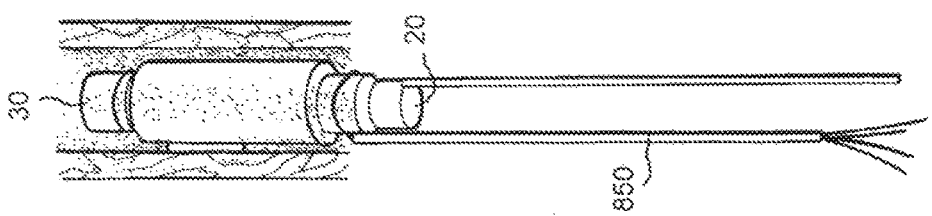
Figure 31B:
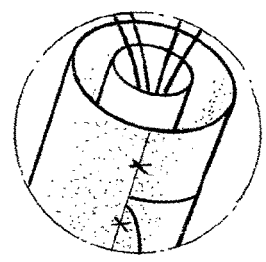
Figure 31A:
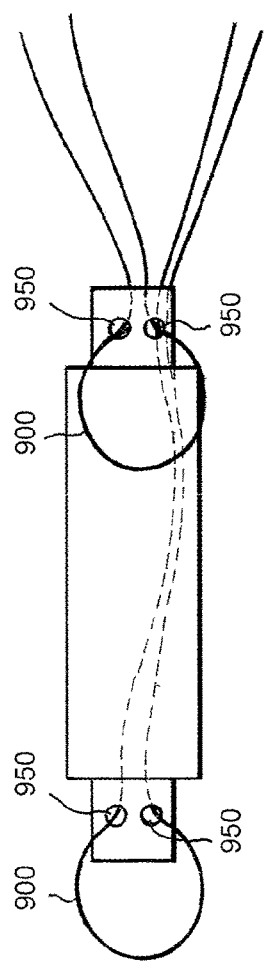
Figure 31D:
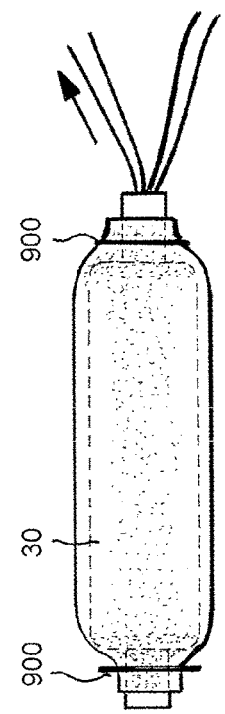
Figure 31C:
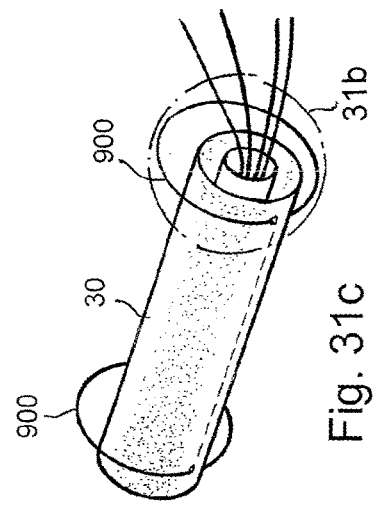

FIGS. 28(a) and 28(b) illustrate exemplary methods for fixing the elongated member relative to the body lumen.

FIGS. 29(a)-29(h) illustrate an exemplary method and apparatus for attaching and detaching the treatment membrane with the delivery device.

FIGS. 30(a)-30(h) illustrate another exemplary method and apparatus for attaching and detaching the treatment membrane with the delivery device.

FIGS. 31(a)-31(d) illustrate another exemplary method and apparatus for attaching and detaching the treatment membrane with the delivery device.

Figure 32B:
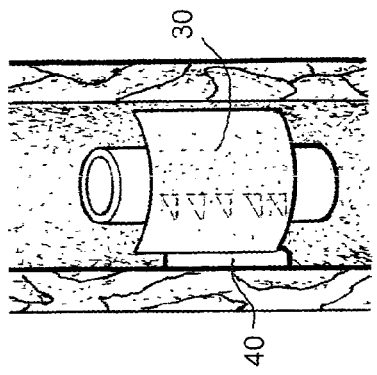
Figure 32C:
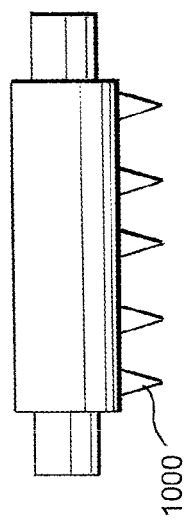
Figure 32A:
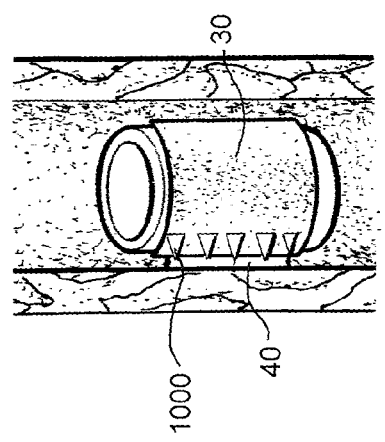

FIGS. 32(a)-32(c) illustrate another exemplary method and apparatus for attaching and detaching the treatment membrane with the delivery device.

DETAILED DESCRIPTION

Set forth below is a detailed description of the method and apparatus for treating urethral stricture disclosed here. The method and apparatus for treating urethral stricture is described and illustrated in terms of several embodiments disclosed as examples of the method and apparatus for treating urethral stricture.

Generally speaking, embodiments of the method involve delivering a treatment membrane, such as buccal mucosa harvested from the inner cheek of the patient, preputium harvested from the patient, or any other biocompatible sheet, to the treatment area of the body lumen, i.e., the area of urethral stricture in the patient's urethra. Prior to delivery of the treatment membrane to the area of the urethral stricture, the area is incised or dilated so that the treatment membrane receives sufficient nutrition for engraftment.

In embodiments of this method of treating the treatment area of the body lumen, i.e., the urethra, an elongated member 10 is inserted into the urethra. In an embodiment, the elongated member 10 is an indwelling catheter, as illustrated in FIG. 1. This elongated member 10 is configured to guide a delivery member 20 which possesses an outer portion on which is mounted a treatment membrane 30. In an embodiment, the treatment membrane 30 is buccal mucosa harvested from the patient's inner cheek.

In an embodiment, the delivery member 20 is then moved to the treatment area 40, e.g., the area of urethral stricture in the patient's urethra. For example, in the FIG. 1 embodiment, the delivery member 20 is slid along the outer surface of the elongated member 10 until it reaches the treatment area. The delivery member 20 includes a fixing member capable of fixing the delivery member 20 to the elongated member 10. In various embodiments discussed in detail below, the fixing member is an expandable member.

Exemplary movements of the elongated member 10 and the delivery member 20 in the insertion and moving steps are illustrated in FIGS. 2(a)-2(b) and in FIGS. 3(a)-3(c). In both procedures, in the step of inserting the elongated member 10 into the urethra, the elongated member 10 carries the delivery member 20 in an insertion direction. In the method of FIGS. 2(a)-2(b), in the step of moving the delivery member 20 to the treatment area 40, the delivery member 20 is moved in the insertion direction, while in the method of FIGS. 3(a)-3(b), in the step of moving the delivery member 20 to the treatment area 40, the delivery member 20 is moved in a direction opposite the insertion direction. Specifically, when the treatment area is located on the bulbar urethra, operator could easily deliver the delivery member by simply pushing the delivery member toward the proximal end of the bulbar urethra which lumen is narrow due to the external urethral sphincter. An X-ray marker can be incorporated into the delivery member 20 so that the operator can determine the position of the delivery member 20 while it is being moved. The delivery member 20 can be moved relative to the elongated member 10 by operating an operation member 50 attached to the delivery member 20. The operation member 50 can be, for example, a wire, a sheath, and/or a tube for inflating the delivery member in embodiments in which the delivery member is inflatable. The operation member 50 can be attached to the delivery member 20, or separate from the delivery member 20, in which case the operation member 50 is used as separate pusher and/or puller of the delivery member 20. In any event, the operation member 50 is configured to be operable by the operator separately from the elongated member 10, such as by having a proximal end which remains outside the urethra.

In an embodiment, the outer portion of the delivery member 20 is pressed against the treatment membrane 30 to contact the treatment membrane 30 with the treatment area for a predetermined period of time. In the FIG. 1 embodiment, the delivery member 20 includes an expandable member comprising an inflatable balloon 60 which is moved to the treatment area, and the step of pressing the outer portion of the delivery member 20 against the treatment membrane 30 comprises expanding the expandable member by inflating the inflatable balloon 60. The expandable member can also be an inflatable sponge, or can operate by mechanical expansion, for example, in the manner of a stent.

After the predetermined period of time, the delivery member 20 is withdrawn from the treatment area. The predetermined time is a sufficient time for the treatment membrane 30, which is buccal mucosa in an embodiment, to graft to the treatment area due to pressure provided by the delivery member 20 and the pre-incision or pre-dilation of the treatment area by a physician.

In the FIG. 1 embodiment, the delivery member 20 includes the expandable member, and so the expandable member is moved to the treatment area at the same time the delivery member 20 is moved to the treatment area 40. When using the apparatus of this embodiment, the step of pressing the outer portion of the delivery member 20 against the treatment membrane 30 comprises expanding the delivery member. Additionally, in this embodiment, after the predetermined period of time, the delivery member is contracted and then the elongated member 10 is moved out of the urethra to carry the delivery member away from the treatment area and out of the urethra.

In an alternative embodiment illustrated in FIGS. 4(a)-4(c), the delivery member 20 is attached to the expandable member. In the embodiment, the delivery member 20 is a curved plate which is attached to an outer surface of the expandable member/inflatable balloon 60. Furthermore, the inflatable balloon 60 is operated and inflated through a balloon guide 70, which is, for example, a tube through which the balloon 60 can be inflated and which has a proximal end which projects out of the urethra so that it can be independently operated by the operator.

In further alternative embodiments, the apparatus can include an expandable member which is an inflatable balloon 60 separate from the delivery member 20. In this case, the expandable member/inflatable balloon 60 can be moved to the treatment area 40 before or after the delivery member 20 is moved to the treatment area 40. Additionally, in this case, to withdraw the delivery member after the predetermined period of time, the expandable member 60, which is either kept at the treatment area 40 while expanded during the predetermined time, or moved back to the treatment area 40 and expanded during or after the predetermined period of time, can be moved out of the urethra to carry the delivery member 20 away from the treatment area 40 and out of the urethra.

FIGS. 5(a)-5(d) illustrate such an embodiment in which, first, the delivery member 20 is slid along the elongated member 10 to the treatment area 40, and then the inflatable balloon 60 is slid along the elongated member 10 to the treatment area 40. The position of the inflatable balloon 60 relative to the delivery member 20 can be determined by, for example, comparing markings on the operation member 50 and the balloon guide 70 which are disposed in relative positions which line up when the delivery member 20 and the inflatable balloon 60 are at the same axial position. These markings can be, for example, X-ray markers on the operation member 50 and the delivery member 20. Alternatively, a structural positioning system, such as a stop on the delivery member 20 configured to engage with the distal end of the inflatable balloon 60 to stop further movement of the inflatable balloon 60 in the distal direction, can be provided for relative positioning of the inflatable balloon 60 relative to the delivery member 20.

In each of the embodiments which includes an expandable member such as an inflatable balloon 60, the apparatus can be configured so that, when the inflatable balloon 60 is expanded, relative sliding movement between the delivery member 20 and the elongated member 10 in the axial direction is prevented by virtue of the inflatable balloon 60 pressing on both the delivery member 20 and the elongated member 10. In each of the embodiments in which the elongated member 10 is a catheter, the catheter's lumen allows urine to pass through the urethra when the inflatable balloon 60 is expanded. Additionally, in each case, to withdraw the delivery member after the predetermined period of time, the operation member 50 is pulled to guide the delivery member 20 away from the treatment area 40 and out of the urethra.

In an alternative embodiment illustrated in FIGS. 6(a)-6(f), the delivery member 20 possesses an inner portion 80 separate from the outer portion which presses against the treatment membrane. This inner portion 80 possesses a protrusion 90 which protrudes inwardly. The elongated member 10 possesses a groove 100 extending in an axial direction of the elongated member 10 and a plurality of spaced-apart notches 110 extend perpendicularly from the groove 100. In use, in the step of moving the delivery member to the treatment area, the protrusion 90 slides within the groove 100 in the axial direction, and after this step, the delivery member is rotated to cause the protrusion 90 to rotate into one of the plurality of notches 110, thereby preventing relative sliding movement between the delivery member and the elongated member in the axial direction. Additionally, the step of pressing the outer portion of the delivery member against the treatment membrane comprises moving the outer portion (which can have a curved plated shape such as shown in the FIG. 4 embodiment) relative to the inner portion 80 of the delivery member having the protrusion. Alternatively, the step of pressing the outer portion of the delivery member against the treatment membrane can comprise expanding an expandable member provided between the elongated member 10 and the delivery member.

FIGS. 7(a)-7(d) illustrate an embodiment in which the expandable member is moved to the treatment area after the delivery member is moved to the treatment area. In this embodiment, an endoscope 120 can be used as the elongated member to monitor the position of the delivery member 20 relative to the treatment area 40, and so in some embodiments using the endoscope 120, x-ray markings are not used. However, some embodiments use both the endoscope 120 and x-ray markings for positioning. Additionally, in this embodiment, after the step of moving the delivery member 20 to the treatment area 40, the elongated member/endoscope 120 is withdrawn from the urethra. An elongated member 10 and inflatable balloon 60 are then moved, either sequentially or simultaneously, to position the inflatable balloon relative to the delivery member 20. The inflatable balloon 60 can be fixed to the elongated member 10 such that the elongated member 10 and inflatable balloon 60 are always moved simultaneously, but this is not required The position of the inflatable balloon 60 relative to the delivery member 20 can be determined by, for example, comparing markings on the operation member 50 and the balloon guide 70 which are disposed in relative positions which line up when the delivery member 20 and the inflatable balloon 60 are at the same axial position. These markings can be, for example, X-ray markers on the operation member 50 and the delivery member 20. Alternatively, a structural positioning system, such as a stop on the delivery member 20 configured to engage with the distal end of the inflatable balloon 60 to stop further movement of the inflatable balloon 60 in the distal direction, can be provided for relative positioning of the inflatable balloon 60 relative to the delivery member 20.

The embodiment of FIGS. 8(a)-8(e) is similar to the embodiment of FIGS. 7(a)-7(d) except that the outer portion of delivery member 20 (which is a curved plate in the embodiment) faces a side of the urethra opposite the treatment area 40. This affords a clear view of the treatment area 40 by the endoscope 120. In this embodiment, after the step of moving the delivery member 20 to the treatment area 40 and before the step of pressing the outer portion of the delivery member 20 against the treatment membrane 30, the delivery member 20 is rotated to a position in which the outer portion of the delivery member 20 faces the treatment area 40.

In the apparatus of the embodiment of FIGS. 9(a)-9(e), a one-way expandable member 150 is used as the delivery member, with the treatment membrane 30 being mounted to this one-way expandable member 150. The one-way expandable member 150 has an annular inner surface that is fixed and an expandable annular outer surface. The one-way expandable member 150 is removably mounted to an expandable intermediate member 160, which is mounted to elongated member/endoscope 120. The expandable intermediate member 160 is a two-way expandable member in that it expands at both its annular inner surface and its annular outer surface.

In the method illustrated in FIGS. 9(a)-9(e), before the step of inserting the elongated member/endoscope 120 into the urethra, the delivery member/one-way expandable member 150 is mounted onto the expandable intermediate member 160 and the elongated member/endoscope 120, and the expandable intermediate member 160 is expanded to prevent relative movement between the delivery member/one-way expandable member 150 and the elongated member/endoscope 120. The elongated member 120 is then moved in the axial direction to move the delivery member 150 and intermediate member 160 to the treatment area 40. The delivery member 150 is then expanded to press the outer portion of the delivery member 150 against the treatment membrane 30, thereby contacting the treatment membrane 30 with the treatment area 40. The intermediate member 160 is then contracted, and the delivery member 150 is dismounted from the intermediate member 160 and the elongated member 120 by pulling back the elongated member 120, which still carries the intermediate member 160, thus leaving the delivery member 150 at the treatment area 40. An indwelling catheter can then be inserted into the delivery member 150 for urine drainage while the delivery member 150 is in position. After the predetermined period of time, which, as discussed above, is a sufficient time for the treatment membrane 30 to graft to the treatment area 40, the steps are reversed, i.e., the indwelling catheter is removed, the intermediate member 160 is moved to the treatment area 40 via the elongated member/endoscope 120 and expanded to prevent relative movement between the delivery member 150 and the elongated member 120, the delivery member 150 is contracted, and then the elongated member 120, with the intermediate member 160 and delivery member 150 mounted thereon, is removed from the urethra. An alternative process for removing the delivery member 150 involves pulling on an operation member, such as an inflation tube (not shown) attached to the delivery member 150 and used for expanding and contracting the delivery member 150.

FIGS. 10(a)-10(e) illustrate an embodiment of a method which uses a similar apparatus as the embodiment of FIG. 9(a)-9(e). However, in the method of FIGS. 10(a)-10(e), when the treatment area 40 is visible through the elongated member/endoscope 120 and before the delivery member 150 and intermediate member 160 reach the treatment area 40, the intermediate member 160 is contracted, and the delivery member 150 is dismounted from the intermediate member 160 and the elongated member 120 and moved to the treatment area 40 via the operation member 50. The delivery member 150 can be moved to the treatment area 40, with the intermediate member 160, or, in alternative embodiment, without the intermediate member 160. The delivery member 150 is then expanded to press the outer portion of the delivery member 150 against the treatment membrane 30, thereby contacting the treatment membrane 30 with the treatment area 40. As in the embodiment of FIGS. 9(a)-9(e), an indwelling catheter is inserted in the delivery member 150 and the delivery member 150 is kept in position for the predetermined period of time and removed after the predetermined period of time. The process for removing the delivery member 150 from the treatment area 40 after the predetermined period of time is the same as that described above with respect to the embodiment of FIGS. 9(a)-9(e) such as by pulling on the unillustrated inflation tube attached the delivery member 150.

In the apparatus of the embodiment of FIGS. 11(a)-11(e), a two-way expandable member 170 is used as the delivery member, with the treatment membrane 30 being mounted to this two-way expandable member 170. The two-way expandable member 170 expands at both its annular inner surface and its annular outer surface. The two-way expandable member 170 is removably mounted to the elongated member/endoscope 120.

In the method illustrated in FIGS. 11(a)-11(e), before the step of inserting the elongated member/endoscope 120 into the urethra, the delivery member/two-way expandable member 170 is mounted onto the elongated member/endoscope 120, and the delivery member/two-way expandable member 170 is expanded to prevent relative movement between the delivery member/two-way expandable member 170 and the elongated member/endoscope 120. The elongated member 120 is then moved in the axial direction to move delivery member/two-way expandable member 170 to the treatment area 40. The delivery member/two-way expandable member 170 is then contracted to allow relative movement between the delivery member/two-way expandable member 170 and the elongated member 120. The elongated member 120 is then pulled back, resulting in dismounting of the delivery member/two-way expandable member 170 from the elongated member/endoscope 120, and then the delivery member/two-way expandable member 170 is again expanded to press the outer portion of the delivery member/two-way expandable member 170 against the treatment membrane 30, thereby contacting the treatment membrane 30 with the treatment area 40. An indwelling catheter is then inserted into the delivery member/two-way expandable member 170. After the predetermined period of time, which, as discussed above, is a sufficient time for the treatment membrane 30 to graft to the treatment area 40, the steps are reversed, i.e., the indwelling catheter is removed, the delivery member/two-way expandable member 170 is contracted, the endoscope/elongated member is then reintroduced into the delivery member/two-way expandable member 170 and the delivery member/two-way expandable member 170 re-expanded, and then the elongated member/endoscope 120, with the delivery member/two-way expandable member 170 mounted thereon, is removed from the urethra. In the embodiment, the delivery member/two-way expandable member 170 may be removed by pulling on the unillustrated inflation tube attached to the delivery member/two-way expandable member.

The method illustrated in FIGS. 12(a)-12(e) is similar to that illustrated in FIGS. 11(a)-11(e) except that the delivery member is a one-way expandable member 180 having a fixed outer surface, i.e., only the inner surface changes size to be able to mount to and dismount from the endoscope 120. The method of use is the same as that illustrated in FIGS. 11(a)-11(e) except that the delivery member/one-way expandable member 180 is not re-expanded after removal of the elongated member/endoscope 120 until after the elongated member/endoscope 120 has been reinserted into the delivery member/one-way expandable member 180 for removal of the delivery member/one-way expandable member 180, or at all in the case in which the delivery member/one-way expandable member 180 is removed by pulling on an unillustrated inflation tube attached to the delivery member/one-way expandable member 180. In this embodiment, the delivery member/one-way expandable member 180 is large enough outer diameter for successful engraftment of the treatment membrane 30 to the treatment area 40.

In embodiments in which the delivery member is an expandable member having an adjustable outer circumference, i.e., an expandable outer surface, in order to mount the treatment membrane 30 to the delivery member/expandable member 200, the treatment membrane 30 is wrapped around the expandable member 200, the opposite overlapped edges of the expandable member 200 are pinched, and then the opposite overlapped edges of the expandable member 200 are attached together by, for example, suturing or heat sealing. FIGS. 13(a)-13(b) illustrate an exemplary process in which the pinching of the opposite overlapped edges of the treatment membrane 30 together is done with a clip part 220 of a clip device 210. Alternatively, the treatment membrane 30 can first be wrapped around a mold and the opposite overlapped edges attached together, then the mold is removed, then the treatment membrane 30 mounted to the expandable member 200.

The circumference of the treatment membrane 30 can be set by setting the circumference of the expandable member 200 to be the desired circumference of the treatment membrane 30. And by using a clip device 210 which includes an indicator 230, such as a ruler which provides an indication of a size of the expandable member 200, as illustrated in FIGS. 14(a)-14(b), the expandable member 200 can be expanded during the mounting process based on the indication. Furthermore, by using a clip device 210 which also includes a limiter 240 which limits the size of the expandable member 200, as illustrated in FIGS. 15(a)-15(b), expansion of the expandable member 200 can be automatically stopped based on a setting of the limiter 240.

As illustrated in FIGS. 16(a)-16(b), the clip device 210 can further include a cavity 250, in which case the method will further include positioning the treatment membrane 30 and the expandable member 200 in the cavity and, if necessary, expanding the expandable member 200 while the treatment membrane 30 and the expandable member 200 are positioned in the cavity 250. In an embodiment, a plurality of clip devices 210 having different sized cavities can be made available, and the circumference of the treatment membrane 30 can be set by selecting the clip device 200 having the appropriately-sized cavity.

The clip device 210 illustrated in FIGS. 16(a)-16(b) also possesses suturing holes 260 configured to align with the opposite overlapped edges of the treatment membrane 30. When such suturing holes 260 are provided, the opposite overlapped edges of the treatment membrane can be attached by performing a suturing operation through the suturing holes 260. The clip device 210 illustrated in FIGS. 16(a)-16(b) further possesses suturing holes 270 configured to align with opposite ends of the treatment membrane 30. When such suturing holes 270 are provided, the opposite ends of the treatment membrane can be at least partially closed by performing a suturing operation through the suturing holes 270. In more detail, as shown in the FIG. 16c view of the bottom of the clip device 210, one suturing hole 270 is provided at each end of the bottom, while as shown in the FIG. 16d view of the bottom of the clip device 210, two suturing holes are provided at each end of the top. A suture passing through the suturing holes 270 of one end of the clip device 210 can tighten that end of the treatment membrane 30 around that end of the expandable member 200. Since, as illustrated in FIG. 13(a), the expandable member 200 can have smaller-circumference ends serving as attachment parts, tightening each end of the treatment membrane 30 around the smaller-circumference ends of the expandable member 200 can serve to immobilize the treatment membrane 30 with respect to the expandable member 200. The treatment membrane 30 can then be released from the expandable member 200 at the appropriate time of the procedure by pulling on the strings which are used to provide the sutures through the suturing holes 270.

In the clip devices 210 described above, the clip part 220 of the clip device 210 possesses two opposed clip portions which are forced together by a spring force. With this configuration, the step of pinching the opposite overlapped edges of the treatment membrane 30 with the clip part 220 comprises providing a force which opposes the spring force to move the opposed clip portions apart, moving the opposite overlapped edges of the treatment membrane 30 to a pinching operation position, and releasing the force which opposes the spring force to allow the spring force to force the opposed clip portions together at the pinching operation position to thereby pinch the opposite overlapped edges.

In an alternative embodiment, a clip device, such as the clip device 280 illustrated in FIGS. 17(a)-17(c), can be provided, in which the clip part comprises completely separable opposed clip portions 290. With such a clip device 280, the step of pinching the opposite overlapped edges of the treatment membrane 30 with the clip part comprises separating the opposed clip portions 290, moving the opposite overlapped edges of the treatment membrane 30 to a pinching operation position, and bringing the opposed clip portions 290 together at the pinching operation position to thereby pinch the opposite overlapped edges. Furthermore, the circumference of the treatment membrane 30 can be selected by selecting opposed clip portions 290 with the appropriately sized cavity portions 300. A spring mechanism can also be used in this embodiment to assist in bringing the opposed clip portions 290 together.

The delivery member can also include attachment parts to assist in attaching and detaching the treatment membrane to and from the delivery device. In the embodiment illustrated in FIGS. 18(a)-18(b), the delivery member/expandable member 200 includes an attachment part 310 at each end, and the opposite edges of the treatment membrane 30 are sutured directly to the attachment parts 310. FIGS. 19(a)-19(d) illustrate a similar embodiment in which the treatment membrane 30 is attached to each attachment part 320 by virtue of suturing opposite edges of the treatment membrane such that openings are defined through which the attachment parts 320 protrude. The curved shape of the attachment parts 320 assists in keeping the treatment membrane 30 attached even though it is not directly sutured to the attachment parts 320 in this embodiment. In these embodiments, the delivery member 200 and attached treatment member 30 can be considered to together constitute a therapeutic device.

Figure 19C:
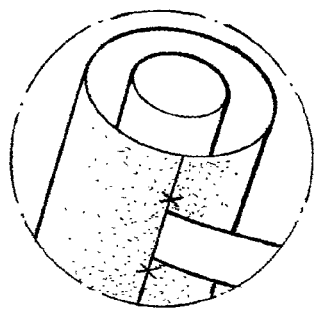
Figure 19B:
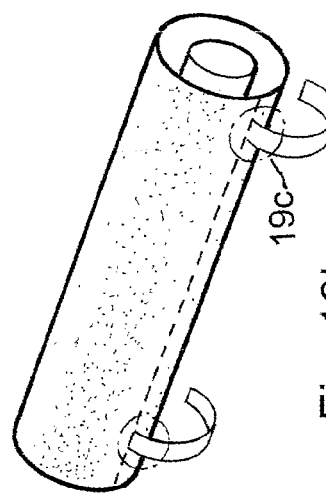
Figure 19A:
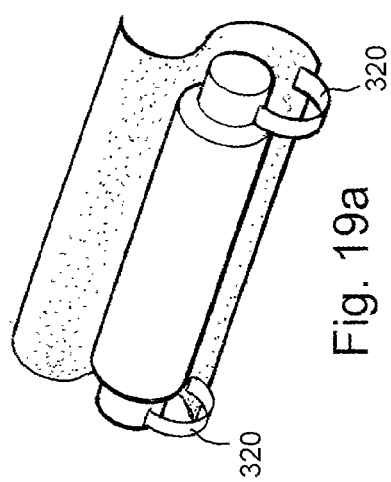
Figure 19D:
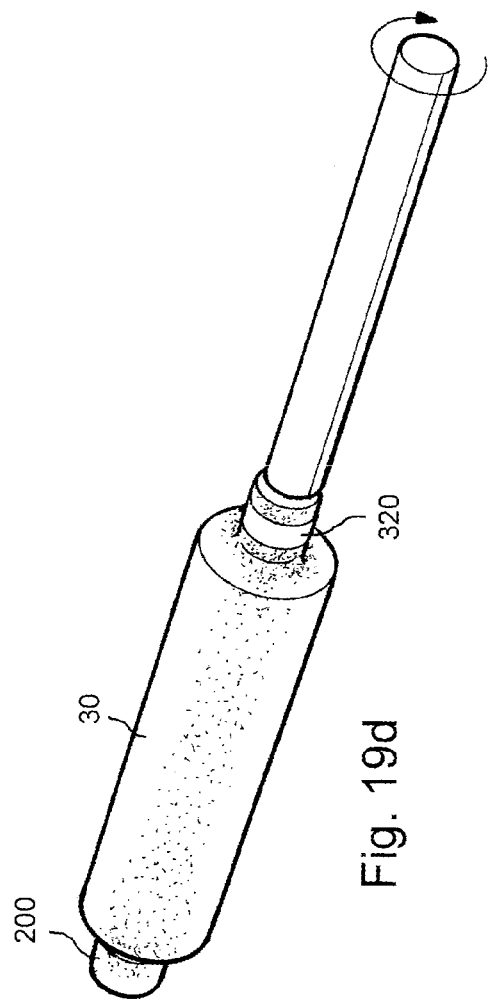

As illustrated in FIG. 19(d), in the embodiment in which curved attachment parts 320 are used, the delivery member 200 be rotated to cause the curved attachment parts to 320 retract through the openings defined by the sutures and thereby detach the treatment membrane 30 from the delivery member 200. The delivery member 200 can then be withdrawn from the urethra. Furthermore, in embodiments in which the delivery member 200 is an expandable member, the expandable member can additionally or alternatively be contracted in the detachment process, as illustrated in FIGS. 20(a) and 20(b).

FIGS. 21(a)-21(c) illustrate a further embodiment in which each attachment part 330 is formed as two oppositely curved portions, and the treatment membrane 30 is detached by rotating the delivery member 200 in first one direction, and then the other direction.

FIG. 22 illustrates an alternative embodiment in which the attachment parts comprise slits 340 in the delivery member 200. Such slits 340 can be configured to engage portions of the treatment membrane 30 or sutures in the treatment membrane 30, and can detach from such portions by rotating the delivery member 200.

Further alternative embodiments of attachment parts include tabs for suturing opposite ends of the treatment membrane thereto illustrated in FIG. 23(a), tips for piercing opposite ends of the treatment membrane as illustrated in FIG. 23(b), hooks for hooking across the treatment membrane as illustrated in FIGS. 23(c) and 23(d), and straight attachment parts, such as those illustrated in FIGS. 18a) and (18b) but provided across the treatment membrane as illustrated in FIG. 23(e). Additionally, the attachment parts can be strings for binding opposite ends of the treatment membrane as illustrated in FIGS. 23(f) and 23(g), suction cups for suctioning opposite ends of the treatment membrane as illustrated in FIG. 23(h), adhesive sheets for adhering to opposite ends of the treatment membrane as illustrated in FIG. 23(i), and suction holes for suctioning across the treatment membrane as illustrated in FIG. 23(j). The various attachment parts can be located on opposite ends of the treatment membrane, across the treatment membrane, or both.

Various methods for ensuring that the delivery member is provided at the delivery area are discussed above. Additional methods which can be adapted to the previously discussed embodiments are illustrated in FIGS. 24-28.

In the method illustrated in FIGS. 24(a)-24(c), prior to insertion of the elongated member and delivery member into the urethra, a measuring member 400, such as a wire or tube with a blunt distal end and measurement markings starting from the distal end, is inserted into the urethra until its distal end reaches the subject's bladder neck 450 (as determined by resistance of the measuring member 400 to further insertion). An endoscope 120 is then used to view the measurement markings next to the treatment area 40. Such measurement markings can be used to determine the length between the bladder neck 450 and the treatment area 40. Next, the delivery member 20 is fixed to the elongated member 10 at an appropriate position based on the known length from the bladder neck 450 to the treatment area 40 which would cause the treatment membrane 30 to line up with the treatment area 40 when the blunt distal portion of the elongated member 10 reaches the bladder neck 450. Measurement markings can be provided on the elongated member 10 for positioning of the delivery member 20 relative to the elongated member 10.

In the method illustrated in FIGS. 25(a)-25(c), prior to insertion of the elongated member and delivery member into the urethra, a measuring member 500, such as a wire or tube or sheath with measurement markings starting from the distal end, is inserted into the urethra until its distal end reaches the treatment area 40, as determined by an endoscope 120. The operator can then use the measurement markings on the measuring member 500 to visually determine the length from the treatment area to the external urethra meatus 550. With this information, the operator can more precisely position the delivery member 20 and treatment membrane 30. For example, in an embodiment in which the elongated member 10 is inserted into the urethra, and then the delivery member 20 moved along the elongated member 10, measurement markings on the operation member 50 can be used to determine that the delivery member 20 has moved within the urethra the same length as the length between the treatment area 40 and the external urethra meatus 550. In this case, the delivery member 20 will have been moved to the treatment area 40. The operator can also determine the length between the treatment area and another anatomical landmark. The anatomical landmark includes, for example, the bladder neck, the external urethra meatus, or the membranous urethra. After these steps, the delivery member 20 is fixed to the elongated member 10 to avoid unexpected movement of the treatment membrane mounted on the delivery member from the treatment area 40 during the predetermined period of time.

The proper positioning of the delivery member 20 can also be monitored by using a clear indwelling catheter for the elongated member 10 and providing an endoscope 120 within the clear indwelling catheter so that the operator can visually determine that the delivery member 20 has been provided at the treatment area. Alternatively, as illustrated in FIGS. 26(a)-26(c), a clear indwelling catheter having measurement markings starting from the blunt distal end can be used as the elongated member 10. In this method, the distance between the bladder neck and the treatment area 40 is first measured, for example, in the manner described with respect to FIG. 24(a). Then, the endoscope 120 can be provided within the inserted elongated member 120 to view the position of the delivery member relative to the measurement markings on the elongated member 120 to help with proper positioning of the delivery member 20 relative to the treatment area 40.

Another type of clear elongated member that can be used as a delivery member is a clear sheath 600, as illustrated in FIGS. 27(a)-27(f). The method in this embodiment is similar to the method used in FIGS. 11(a)-11(f) except that, instead of being mounted directly to the endoscope 120, the delivery member 170 is mounted to the clear sheath 600, and the endoscope 120 is positioned within the clear sheath 600 to view the position of the delivery member 170 relative to the treatment area 40. When the endoscope 120 is withdrawn, the clear sheath 600 remains. After the indwelling catheter 650 is inserted into the clear sheath 600 and the delivery member 170, the clear sheath 600 is withdrawn.

FIGS. 28(a) and 28(b) illustrate methods for fixing the position of the elongated body/indwelling catheter 10 relative to the treatment area 40. In FIG. 28(a), a stopper 700 is fixed to the appropriate position on the elongated body/indwelling catheter 10 to engage with the external urethra meatus. In more general terms, the elongated body 10 is fixed to at least one side of the edge of the body lumen. This can also be accomplished by suturing the external urethra meatus to the side of the elongated body 10, as illustrated in FIGS. 28(b). Additionally or alternatively, the distal end of the elongated body/indwelling catheter 10 can be fixed relative to the bladder neck 450 by, for example, hooking or hanging. Fixation of the delivery member 20 to the elongated body/indwelling catheter 10 further ensure to avoid unexpected movement of the treatment membrane mounted on the delivery member from the treatment area 40 during the predetermined period of time.

FIGS. 29(a)-29(h) and 30(a)-30(h) illustrate alternative methods of attaching and detaching the treatment membrane 30 with the delivery member 20 using a snare device. In FIGS. 29(a)-29(h), the snare device 800 is a string extending back and forth through a pipe and looped at one end. Pushing and pulling the string at the other end of the pipe increases and decreases the size of the loop. In the illustrated embodiment, the loop is provided around the distal end of the treatment membrane and pulled tight to contract that end of the treatment membrane around one of the smaller-circumference ends of the delivery member (the distal end in the embodiment). At the appropriate time, the loop is expanded to detach the treatment membrane 30 from the delivery member 20. In the method of FIGS. 30(a)-30(h), a snare device 850 having two loops to snare both smaller-diameter ends of the delivery member 20 is used. In this embodiment, as an alternative to expanding the loops to detach the treatment membrane 30 from the delivery member 20, the loops can instead be cut.

Alternatively, as illustrated in FIGS. 31(*a*)-31(*c*), snare loops 900 can be formed by providing openings 950 in the smaller-circumference ends of the delivery member 20 and running strings through the respective sets of openings 950. By pulling both strings for a particular loop, that loop can be tightened to attached the treatment membrane 30 to the delivery member 20. At the appropriate time, a single string for each loop can be pulled to remove the strings entirely and allow the treatment membrane 30 to detach from the delivery member.

As a further alternative, one or more puncturing members 1000 can be provided on the delivery member 20, as shown in FIGS. 32(*a*)-32(*c*). When the delivery member 20 is expanded, the puncturing devices 1000 puncture the treatment membrane to attached the treatment membrane 30 to the delivery member 20. The puncturing devices 1000 can also be configured to puncture the wall of the urethra. In this embodiment, in order to detach the treatment membrane 30, the delivery member 20 is contracted to pull the puncture devices 1000 out of the treatment membrane 30 and/or the wall of the urethra.

The detailed description above describes features and aspects of embodiments of a trans-urethral urethroplasty method and apparatus disclosed by way of example. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. A method of delivering a therapeutic device to a treatment area of a body lumen, the therapeutic device comprising a) a delivery member possessing at least one attachment part, and b) a treatment membrane, the method comprising:

wrapping the treatment membrane on the delivery member;

suturing edges of the treatment membrane together in a manner in which an unsutured axial section between the sutured edges defines an opening through which the attachment part protrudes;

attaching the treatment membrane to the attachment part of the delivery member; and moving the delivery member with the treatment membrane attached thereto within the body lumen toward the treatment area.

2. The method of claim 1, wherein the delivery member has a first end and a second end, each of which possesses at least one attachment part.

3. The method of claim 1, wherein the method is a method of treating urethral stricture.

4. The method of claim 1, wherein the treatment area is urethral stricture of a urethra.

5. A method of delivering a therapeutic device to a treatment area of a body lumen, the therapeutic device comprising a) a delivery member possessing at least one attachment part, and b) a treatment membrane attached to the delivery member, the method comprising:

moving the delivery member with the treatment membrane attached thereto within the body lumen toward the treatment area;

detaching the treatment membrane from the delivery member; and withdrawing the delivery member from the body lumen, wherein the step of detaching the treatment membrane from the delivery member comprises rotating the delivery member to cause the attachment part to withdraw from an opening defined by an unsutured axial section between sutured edges of the treatment membrane.

6. The method of claim 5, wherein the method is a method of treating urethral stricture.

7. The method of claim 5, wherein the treatment area is urethral stricture of a urethra.

8. The method of claim 5, wherein the delivery member has a first end and a second end, each of which possesses at least one attachment part.

* * * * *